United States Patent [19]
Bell et al.

[11] Patent Number: 5,426,107
[45] Date of Patent: Jun. 20, 1995

[54] PYRAZOLOPYRIMIDINONE ANTIANGINAL AGENTS

[75] Inventors: Andrew S. Bell; Nicholas K. Terrett, both of Groton, Conn.

[73] Assignee: Pfizer Inc., New York, N.Y.

[21] Appl. No.: 96,743

[22] Filed: Jul. 23, 1993

Related U.S. Application Data

[62] Division of Ser. No. 897,735, Jun. 12, 1992, Pat. No. 5,272,147.

[30] Foreign Application Priority Data

Jul. 9, 1991 [GB] United Kingdom ................ 9114760

[51] Int. Cl.$^6$ ............................................. A61K 31/505
[52] U.S. Cl. ................... 514/234.2; 514/253; 514/258
[58] Field of Search ....................... 514/234.2, 253, 258

[56] References Cited

U.S. PATENT DOCUMENTS

| | | | |
|---|---|---|---|
| 3,036,070 | 5/1962 | Druey et al. | 544/262 |
| 3,600,689 | 8/1971 | Druey et al. | 544/118 |
| 4,052,390 | 10/1977 | Broughton | 514/258 |
| 4,167,568 | 9/1979 | Knowles et al. | 514/258 |
| 4,666,908 | 5/1987 | Hamilton | 544/118 |
| 5,075,310 | 12/1991 | Coates | 514/258 |
| 5,250,534 | 10/1993 | Bell et al. | 514/258 |
| 5,346,901 | 9/1994 | Bell et al. | 514/258 |

FOREIGN PATENT DOCUMENTS

| | | |
|---|---|---|
| 1095688 | 1/1988 | Australia . |
| 3309689 | 4/1989 | Australia . |
| 0347146 | 6/1989 | European Pat. Off. . |
| 0349239 | 6/1989 | European Pat. Off. . |
| 0351058 | 6/1989 | European Pat. Off. . |
| 0352960 | 7/1989 | European Pat. Off. . |
| 0371731 | 11/1989 | European Pat. Off. . |
| 0463756 | 1/1992 | European Pat. Off. . |

OTHER PUBLICATIONS

Hamilton, Journal of Medicinal Chemistry, 30, 1987, 91-96.

Tokyo Koho, Chem. Abs. vol. 106, Entry 101967h, Abstracting Japan 61-236778 (1987).

Primary Examiner—Donald G. Daus
Attorney, Agent, or Firm—Peter C. Richardson; Gregg C. Benson; Robert T. Ronau

[57] ABSTRACT

Compounds of the formula

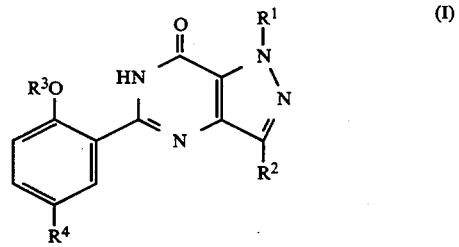

and pharmaceutically acceptable salts thereof are selective cGMP PDE inhibitors which are useful in the treatment of such diseases and adverse conditions as angina, hypertension, congestive heart failure, reduced blood vessel patency, peripheral vascular disease, stroke, bronchitis, chronic asthma, allergic asthma, allergic rhinitis, glaucoma, and diseases characterized by disorders of gut motility.

2 Claims, No Drawings

PYRAZOLOPYRIMIDINONE ANTIANGINAL AGENTS

This is a division of application Ser. No. 07/897,735, filed on Jun. 12, 1992, entitled "Pyrazolopyrimidinone Antianginal Agents," now U.S. Pat. No. 5,272,147.

BACKGROUND OF THE INVENTION

This invention relates to a series of pyrazolo[4,3-d]-pyrimidin-7-ones, which are potent and selective inhibitors of cyclic guanosine 3′,5′-monophosphate phosphodiesterase (cGMP, PDE), having utility in a variety of therapeutic areas including the treatment of various cardiovascular disorders such as angina, hypertension, heart failure and atherosclerosis.

The compounds of the invention exhibit selectivity for inhibition of cGMP PDEs rather than cyclic adenosine 3′,5′-monophosphate phosphodiesterases (cAMP PDEs) and, as a consequence of this selective PDE inhibition, cGMP levels are elevated, which in turn can give rise to beneficial anti-platelet, anti-neutrophil, anti-vasospastic and vasodilatory activity, as well as potentiation of the effects of endothelium-derived relaxing factor (EDRF) and nitrovasodilators. Thus the compounds have utility in the treatment of a number of disorders, including stable, unstable and variant (Prinzmetal) angina, hypertension, pulmonary hypertension, congestive heart failure, atherosclerosis, conditions of reduced blood vessel patency e.g. post-percutaneous transluminal coronary angioplasty (post-PTCA), peripheral vascular disease, stroke, bronchitis, chronic asthma, allergic asthma, allergic rhinitis, glaucoma, and diseases characterised by disorders of gut motility, e.g. irritable bowel syndrome (IBS).

European patent application EP-A-0201188 discloses certain pyrazolo[4,3-d]pyrimidin-7-ones as adenosine receptor antagonists and PDE inhibitors, useful in the treatment of cardiovascular disorders such as heart failure or cardiac insufficiency. However these compounds are neither particularly potent PDE inhibitors, nor are they reported to be selective inhibitors of cGMP PDE.

SUMMARY OF THE INVENTION

The compounds of the present invention have the formula (I):

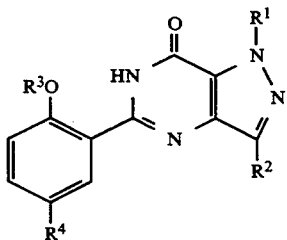

(I)

wherein
$R^1$ is H; $C_1$-$C_3$ alkyl optionally substituted with one or more fluoro substituents; or $C_3$-$C_5$ cycloalkyl;
$R^2$ is H, or $C_1$-$C_6$ alkyl optionally substituted with one or more fluoro substituents or with $C_3$-$C_6$ cycloalkyl;
$R^3$ is $C_1$-$C_6$ alkyl optionally substituted with one or more fluoro substituents or with $C_3$-$C_6$ cycloalkyl;
$C_3$-$C_5$ cycloalkyl; $C_3$-$C_6$ alkenyl; or $C_3$-$C_6$ alkynyl;
$R^4$ is $C_1$-$C_4$ alkyl optionally substituted with OH, $NR^5R^6$, CN, $CONR^5R^6$ or $CO_2R^7$; $C_2$-$C_4$ alkenyl optionally substituted with CN, $CONR^5R^6$ or $CO_2R^7$; $C_2$-$C_4$ alkanoyl optionally substituted with $NR^5R^6$; hydroxy $C_2$-$C_4$ alkyl optionally substituted with $NR^5R^6$; ($C_2$-$C_3$ alkoxy)$C_1$-$C_2$ alkyl optionally substituted with OH or $NR^5R^6$; $CONR^5R^6$; $CO_2R^7$; halo; $NR^5R^6$; $NHSO_2NR^5R^6$; $NHSO_2R^8$; or phenyl or heterocyclyl either of which is optionally substituted with methyl;
$R^5$ and $R^6$ are each independently H or $C_1$-$C_4$ alkyl, or together with the nitrogen atom to which they are attached form a pyrrolidinyl, piperidino, morpholino, 4-($NR^9$)-piperazinyl or imidazolyl group wherein said group is optionally substituted with methyl or hydroxy;
$R^7$ is H or $C_1$-$C_4$ alkyl;
$R^8$ is $C_1$-$C_3$ alkyl optionally substituted with $NR^5R^6$; and
$R^9$ is H; $C_1$-$C_3$ alkyl optionally substituted with phenyl; hydroxy $C_2$-$C_3$ alkyl; or $C_1$-$C_4$ alkanoyl;
and pharmaceutically acceptable salts thereof.

In the above definition, unless otherwise indicated, alkyl groups having three or more carbon atoms may be straight or branched chain. In addition alkenyl or alkynyl groups having four or more carbon atoms, or alkoxy groups having three carbon atoms, may be straight or branched chain. Halo means fluoro, chloro, bromo or iodo, whilst heterocyclyl is selected from thienyl, pyridyl, pyrazolyl, imidazolyl, triazolyl, oxazolyl, thiazolyl or pyrimidinyl.

The compounds of formula (I) may contain one or more asymmetric centres and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of formula (I) may also exist in tautomeric forms and the invention includes both mixtures and separate individual tautomers.

Also included in the invention are radiolabelled derivatives of compounds of formula (I) which are suitable for biological studies.

The pharmaceutically acceptable salts of the compounds of formula (I) which contain a basic centre are acid addition salts formed with pharmaceutically acceptable acids. Examples include the hydrochloride, hydrobromide, sulphate or bisulphate, phosphate or hydrogen phosphate, acetate, benzoate, succinate, fumarate, maleate, lactate, citrate, tartrate, gluconate, methanesulphonate, benzenesulphonate and p-toluenesulphonate salts. Compounds of the formula (I) can also provide pharmaceutically acceptable metal salts, in particular alkali metal salts, with bases. Examples include the sodium and potassium salts.

A preferred group of compounds of formula (I) is that wherein $R^1$ is H, methyl or ethyl; $R^2$ is $C_1$-$C_3$ alkyl; $R^3$ is $C_2$-$C_3$ alkyl; $R^4$ is $C_1$-$C_2$ alkyl optionally substituted with OH, $NR^5R^6$, $CONR^5R^6$ or $CO_2R^7$; acetyl optionally substituted with $NR^5R^6$; hydroxyethyl substituted with $NR^5R^6$; ethoxymethyl optionally substituted with OH or $NR^5R^6$; CH=CHCN; CH=CHCONR$^5$R$^6$; CH=CHCO$_2$R$^7$; CO$_2$H; CONR$^5$R$^6$; Br; NR$^5$R$^6$; NHSO$_2$NR$^5$R$^6$; NHSO$_2$R$^8$; or pyridyl or imidazolyl either of which is optionally substituted with methyl; $R^5$ and $R^6$ are each independently H, methyl or ethyl, or together with the nitrogen atom to which they are attached form a piperidino, morpholino, 4-($NR^9$)-1-piperazinyl or imidazolyl group wherein said group is optionally substituted with methyl or hydroxy; $R^7$ is H or t-butyl; $R^8$ is methyl or $CH_2CH_2CH_2NR^5R^6$; and $R^9$ is H, methyl, benzyl, 2-hydroxyethyl or acetyl.

A particularly preferred group of compounds of formula (I) is that wherein $R^1$ is methyl; $R^2$ is n-propyl; $R^3$ is ethyl or n-propyl; $R^4$ is $CH_2NR^5R^6$, $CH_2OCH_2CH_2NR^5R^6$, $CH_2OCH_2CH_3$, $CH_2OCH_2C-H_2OH$, $COCH_2NR^5R^6$, $CH(OH)CH_2NR^5R^6$, $CH=CHCON(CH_3)_2$, $CH=CHCO_2R^7$, $CO_2H$, $CONR^5R^6$, Br, $NHSO_2NR^5R^6$, $NHSO_2CH_2CH_2CH_2NR^5R^6$, 2-pyridyl, 1-imidazolyl or 1-methyl-2-imidazolyl; $R^5$ and $R^6$ together with the nitrogen atom to which they are attached form a piperidino, 4-hydroxypiperidino, morpholino, 4-($NR^9$)-1-piperazinyl or 2-methyl-1-imidazolyl group; $R^7$ is H or t-butyl; and $R^9$ is H, methyl, benzyl, 2-hydroxyethyl or acetyl.

Especially preferred individual compounds of the invention include:

5-[2-ethoxy-5-(1-methyl-2-imidazolyl)phenyl]-1-methyl-3-n-propyl-1,6-dihydro-7H-pyrazolo[4,3-d]pyrimidin-7-one;

5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one;

5-[5-(4-acetyl-1-piperazinyl)acetyl-2-ethoxyphenyl]-1-methyl-3-n-propyl-1,6-dihydro-7H-pyrazolo[4,3-d]pyrimidin-7-one;

5-(2-ethoxy-5-morpholinoacetylphenyl)-1-methyl-3-n-propyl-1,6-dihydro-7H-pyrazolo[4,3-]pyrimidin-7-one;

and 5-(5-morpholinoacetyl-2-n-propoxyphenyl)-1-methyl-3-n-propyl-1,6-dihydro-7H-pyrazolo[4,3-d]pyrimidin-7-one.

DETAILED DESCRIPTION OF THE INVENTION

Depending on the nature of $R^4$, the compounds of formula (I) may be prepared by a variety of methods from a compound of formula (II):

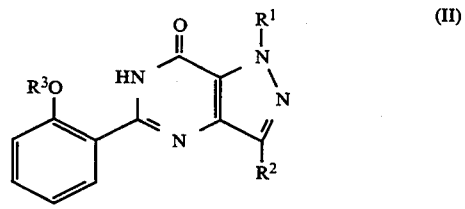

wherein $R^1$, $R^2$ and $R^3$ are as previously defined. For example, when $R^4$ is $C_2$–$C_4$ alkanoyl, the required product is obtainable by conventional Friedel-Crafts acylation whereby (II) is reacted with about a 2-fold excess of an acyl halide of formula ($C_1$–$C_3$ alkyl)COY, wherein Y is halo, preferably chloro or bromo, in the presence of about a 3-fold excess of a Lewis acid such as aluminium chloride or aluminium bromide, in a suitable solvent, e.g. dichloromethane, at from about 0° C. to the reflux temperature of the reaction medium. When $R^4$ is $C_2$–$C_4$ alkanoyl substituted with $NR^5R^6$, wherein $R^5$ and $R^6$ are as previously defined, the product is obtained from (II) via the intermediacy of the corresponding haloketone, i.e. a compound of formula (I) wherein $R^4$ is $CO(C_1$–$C_3$ alkylene)X and X is halo, preferably chloro or bromo, by reaction of the appropriate haloketone with the required amine of formula $R^5R^6NH$ in the presence of at least one equivalent of base to scavenge the liberated acid by-product (HX), in a suitable solvent, e.g. acetonitrile, at about room temperature. The base may be an inorganic salt such as anhydrous potassium carbonate, a tertiary amine such as triethylamine, or excess reactant amine. In cases wherein either $R^5$ or $R^6$ is H, it may be advantageous to use a protected amine of formula $R^5NHP$ or $R^6NHP$ wherein P is a compatible protecting group, e.g. benzyl which can be subsequently removed by catalytic hydrogenation. When both $R^5$ and $R^6$ are H, an ammonia equivalent of formula $P'_2NH$, wherein P' is a protecting group such as t-butoxycarbonyl, may be beneficially employed. In this case, the potassium salt of the non-basic aminating reagent is used for reaction with the haloketone; deprotection is effected by acidolysis using, for example, hydrogen chloride, which allows convenient isolation of the desired aminoketone as its hydrochloric salt. The intermediate haloketone is also obtained via Friedel-Crafts chemistry, as described above, in this case between (II) and the appropriate haloacyl halide of formula X($C_1$–$C_3$ alkylene)COY, wherein X and Y are as previously defined.

The above ketones of general formula (IA);

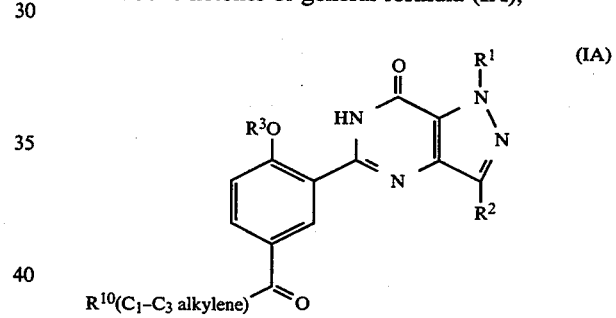

wherein $R^{10}$ is either H or $NR^5R^6$, and $R^1$, $R^2$, $R^3$, $R^5$ and $R^6$ are as previously defined, may be reduced to provide the corresponding alcohol derivatives of general formula (IB):

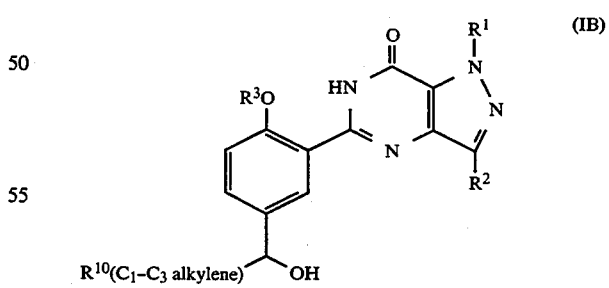

wherein $R^1$, $R^2$, $R^3$ and $R^{10}$ are as previously defined. The reducing agent is preferably sodium borohydride and the reaction may be conducted in a suitable solvent, e.g. ethanol, at about room temperature.

A compound of formula (I) wherein $R^4$ is hydroxymethyl and $R^1$, $R^2$ and $R^3$ are as previously defined may be prepared by subjecting a compound of formula (II) to standard chloromethylation conditions, e.g. paraformaldehyde and concentrated hydrochloric acid, at from about room temperature to about 120° C., to provide the intermediate chloromethyl derivative of formula (III), which is then treated with an alkali metal hydroxide, e.g. sodium hydroxide or potassium hydroxide, in a suitable solvent such as an ethylene glycol-dimethyl sulphoxide mixture at from about room temperature to about 100° C.

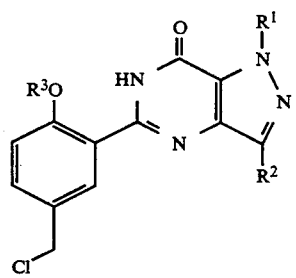

(III)

The above chloromethyl derivatives (III), wherein $R^1$, $R^2$ and $R^3$ are as previously defined, are valuable intermediates in the synthesis of further compounds of formula (I). For example, treatment of (III) with $C_2$- or $C_3$-alkanol in the presence of about one equivalent of an alkali metal, preferably sodium, at about room temperature, affords the corresponding $C_2$- or $C_3$-alkoxymethyl derivatives respectively. Similarly, when a $C_2$- or $C_3$-diol is employed, the analogous hydroxy($C_2$- or $C_3$-alkoxy)methyl compounds are obtained. The latter may be further transformed by activation of the terminal hydroxy group, e.g. by conventional mesylation using about a 10% excess of mesyl chloride, in pyridine as solvent, at from about 0° C. to about room temperature, followed by reaction of the mesylate with, for example, an amine of formula $R^5R^6NH$. Preferably the reaction is conducted with up to a 5-fold excess of amine in a suitable solvent, e.g. acetonitrile, at the reflux temperature of the reaction medium. As discussed above, when either $R^5$ or $R^6$ is H or both are H, an amine protection-deprotection strategy may be profitably employed. Thus are provided compounds of formula (I) wherein $R^4$ is ($C_2$-$C_3$)alkyoxymethyl optionally substituted with either CH or $NR^5R^6$, and $R^1$, $R^2$, $R^3$, $R^5$ and $R^6$ are as previously defined.

The higher homologues of the above compounds, i.e. those compounds of formula (I) wherein $R^4$ is ($C_2$-$C_3$)alkoxyethyl optionally substituted with either OH or $NR^5R^6$, may be synthesised by similar procedures from the 2-chloroethyl, 2-bromoethyl or 2-mesyloxyethyl analogues of (III) which, in turn, are derivable from the corresponding 2-hydroxyethyl precursor by standard procedures. This precursor may be prepared for example from a compound of formula (I), wherein $R^4$ is bromo and $R^1$, $R^2$ and $R^3$ are as previously defined (formula (IV)), by lithium-bromine exchange using n-butyllithium, followed by reaction of the aryllithium intermediate (vide infra) with ethylene oxide.

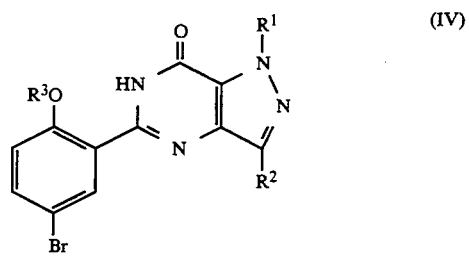

(IV)

The chloromethyl intermediates of formula (III) may also be used for the preparation of compounds of formula (I), wherein $R^4$ is $CH_2NR^5R^6$ and $R^1$, $R^2$, $R^3$, $R^5$ and $R^6$ are as previously defined, by reaction with the appropriate amine of formula $R^5R^6NH$ (or protected version thereof—vide supra). Preferably the reaction is carried out with about a 3-fold excess of amine in a suitable solvent, e.g. 2-butanone, at from about 0° C. to the reflux temperature of the reaction medium. By analogy, compounds of formula (I) wherein $R^4$ is ($C_2$-$C_4$ alkylene)$NR^5R^6$ may be conveniently obtained from the appropriate chloro, bromo, or mesyloxy precursor which, in turn, is derivable from the corresponding alcohol (see above for a synthetic approach to the 2-hydroxyethyl analogue). The 3-hydroxypropyl and 4-hydroxybutyl analogues may be prepared by catalytic hydrogenation of the alkenols obtained when the above-mentioned bromo compound of formula (IV) is subjected to Heck reaction conditions (vide infra) with allyl alcohol or 3-buten-1-ol respectively.

The chloromethyl intermediates may further be employed to furnish the corresponding methyl derivatives, i.e. compounds of formula (I) wherein $R^4$ is $CH_3$ and $R^1$, $R^2$ and $R^3$ are as previously defined. This can be achieved by catalytic hydrogenation using a palladium on charcoal catalyst, in a suitable solvent such as ethyl acetate, at about 50 p.s.i. (3.45 bar) and room temperature. By analogy, when $R^4$ is ethyl, n-propyl or n-butyl, such compounds of formula (I) may also be obtained from the corresponding alkyl chlorides derived, in turn, from the appropriate alcohols mentioned above by standard methodology. Other alcohol derivatives, e.g. the corresponding bromide or mesylate, may also be used.

The above bromo derivatives (IV), which are valuable intermediates in the synthesis of yet further compounds of formula (I), may be prepared from a compound of formula (II) by direct bromination in a suitable solvent. This may be achieved, for example, either with about a 60% excess of N-bromosuccinimide in dimethylformamide at room temperature or with a similar excess of bromine in glacial acetic acid at from about room temperature to about 100° C. Alternatively, (IV) and the corresponding fluoro, chloro and iodo analogues may be obtained from the primary amine (vide infra) via classical sequential diazotisation-halogenation procedures including, for example, the Schiemann, Sandmeyer and Gatterman reactions.

By exploitation of Heck methodology, the bromo intermediate (IV) can be transformed to compounds of formula (I), wherein $R^4$ is CH=CHCN, CH=CHCONR$^5$R$^6$ or CH=CHCO$_2$R$^7$ and R$^1$, R$^2$, R$^3$, R$^5$, R$^6$ and R$^7$ are as previously defined, by employment of acrylonitrile or the appropriate acrylic acid amide or ester derivative. The reaction is generally carried out with about a 50% excess of both the alkene reagent and a tertiary amine such as triethylamine, in the presence of about 0.1 equivalents of a tertiary arylphosphine, preferably tri-o-tolylphosphine, and about 0.05 equivalents of palladium(II) acetate, in a suitable solvent such as acetonitrile at the reflux temperature of the reaction medium. The resulting acrylic esters may be hydrolysed if desired, e.g. using aqueous sodium hydroxide solution, with methanol as co-solvent, to afford the corresponding cinnamic acids. Moreover, all the alkenyl products thus synthesised may be subjected to catalytic hydrogenation, e.g. using 5% palladium on charcoal in a suitable solvent at about 15 p.s.i. (1.0 bar) and room temperature, to provide compounds of formula (I) wherein $R^4$ is $CH_2CH_2CN$, $CH_2CH_2CONR^5R^6$ or $CH_2CH_2CO_2R^7$ and $R^1$, $R^2$, $R^3$, $R^5$, $R^6$ and $R^7$ are as previously defined for formula (I). An alternative reduction strategy, in which the acrylonitrile derivative (cinnamonitrile analogue) is exhaustively hydrogenated with Raney nickel in glacial acetic acid, affords a compound of formula (I) wherein $R^4$ is 3-aminopropyl and $R^1$, $R^2$ and $R^3$ are as previously defined.

The higher homologues, i.e. compounds of formula (I) wherein $R^4$ is either $C_3$-$C_4$ alkyl or $C_3$-$C_4$ alkenyl substituted with CN, $CONR^5R^6$ or $CO_2R^7$, or is 4-aminobutyl, may be derived from the previously mentioned alkenols obtained from Heck reactions between the bromo compound of formula (IV) and either allyl alcohol or 3-buten-1-ol. The conventional procedures necessary for transformation of the terminal hydroxyl group via a suitably reactive derivative, e.g. the corresponding chloride, bromide or mesylate, to the required functional groups will be well known to persons skilled in the art, and will be equally applicable to the 2-hydroxyethyl analogue (vide supra) thereby offering an alternative to Heck methodology. Compounds of formula (I), wherein $R^4$ is $CH_2CN$, $CH_2CONR^5R^6$, $CH_2CO_2R^7$ or $CH_2CH_2NH_2$, may be obtained from the chloromethyl intermediates of formula (III) by reaction with an alkali metal cyanide, e.g. sodium cyanide or potassium cyanide, followed by standard transformations of the resulting nitrile.

As a general alternative to the above Heck reaction approach, the desired alkenes (and derived alkanes via catalytic hydrogenation) may be obtained using a Wittig-Horner strategy in which an aldehyde of formula (I), wherein $R^4$ is CHO and $R^1$, $R^2$ and $R^3$ are as previously defined, is reacted with the appropriate phosphonium salt or phosphonate in the presence of a suitable base. The aldehyde itself is obtainable by formylation, e.g. using dimethylformamide, of the previously described aryllithium derivative of (IV) and, by analogy, is also a convenient precursor to compounds of formula (I) wherein $R^4$ is $C_2$-$C_4$ alkenyl or $C_2$-$C_4$ alkyl and $R^1$, $R^2$ and $R^3$ are as previously defined.

This aryllithium intermediate is also useful in the preparation of compounds of formula (I) wherein $R^4$ is $CONR^5R^6$ or $CO_2R^7$ and $R^1$, $R^2$, $R^3$, $R^5$, $R^6$ and $R^7$ are as previously defined. For example, lithiation of (IV) in dry tetrahydrofuran at about −78° C. using about a 5-fold excess of a solution of n-butyllithium in hexane, quenching of the resulting aryllithium with carbon dioxide at about −40° C., and aqueous work-up at about 0° C. including careful acidification to pH 3, furnishes the corresponding benzoic acid derivative. The acid may be activated under mild conditions, such as those obtaining in peptide bond formation via amino acid coupling procedures, and converted to an ester or amide derivative as required. For example, activation of the benzoic acid using a carbodiimide/1-hydroxybenzotriazole combination in the presence of the required amine of formula $R^5R^6NH$ or alcohol of formula $R^7OH$, in a suitable solvent such as dichloromethane at about 0° C. to room temperature, yields the corresponding amide or ester respectively.

The bromo intermediates o formula (IV) are also of utility in the synthesis of compounds of formula (I) wherein $R^4$ is phenyl or heterocyclyl, each of which is optionally substituted with methyl, and $R^1$, $R^2$ and $R^3$ are as previously defined. When $R^4$ is phenyl or C-linked heterocyclyl, it may be introduced via palladium-catalysed coupling of the zincate derivative generated in situ from the corresponding phenyllithium or heterocyclyllithium intermediate; the latter, in turn, may be obtained from either the heterocycle or haloheterocycle as necessary by treatment with n-butyllithium. Thus, for example, the phenyllithium or heterocyclyllithium (in the presence of about 1 extra equivalent of n-butyllithium to accommodate the active hydrogen atom of the pyrazolopyrimidinone substrate) is treated with about 2 equivalents of anhydrous zinc chloride in dry tetrahydrofuran at about −78° C. followed, at about room temperature, by (IV) and the palladium catalyst, preferably tetrakis(triphenylphosphine)palladium(0). The reaction mixture can be heated to reflux with addition of up to about 2 further equivalents of anhydrous zinc chloride if necessary. When $R^4$ is N-linked heterocyclyl, the reaction may be conducted with up to about a 5-fold excess of the appropriate heterocycle in the presence of about a 10% excess of base, e.g. anhydrous potassium carbonate, to scavenge the hydrogen bromide by-product, together with about a 10% excess of copper-bronze and about 0.25 equivalents of iodine catalyst in a suitable solvent, e.g. dimethylformamide, at about the reflux temperature of the reaction medium.

Compounds of formula (I), wherein $R^4$ is $NHSO_2NR^5R^6$ or $NHSO_2R^8$ and $R^1$, $R^2$, $R^3$, $R^5$, $R^6$ and $R^8$ are as previously defined, may be synthesised from the corresponding primary amine which, in turn, is obtained by nitration of (II) using, e.g. a conventional concentrated nitric acid/concentrated sulphuric acid combination, followed by reduction of the nitroarene by catalytic hydrogenation using conventional procedures. The reaction is generally carried out using equimolar quantities of the primary amine of formula (I), wherein $R^4$ is $NH_2$ and $R^1$, $R^2$ and $R^3$ are as previously defined, and either the required sulphamoyl halide or alkylsulphonyl halide (preferably the chlorides) of formula $R^5R^6NSO_2$halo or $R^8SO_2$halo respectively, in the presence of excess tertiary amine such as triethylamine or pyridine to scavenge the acid by-product, in a suitable solvent, e.g. dichloromethane, at from about 0° C. to about room temperature. Pyridine may conveniently function as both base and solvent when desired, and the reaction may be optionally catalysed by the addition of about 0.1 to 0.2 equivalents of a 4-t-aminopyridine such as 4-dimethylaminopyridine. When both $R^5$ and $R^6$ are H, the desired product may also be obtained by reaction of the primary amine with sulphamide in a suitable solvent, e.g. 1,4-dioxan, at about 100° C.

When, in transformations of compounds of formula (II) to compounds of formula (I), $R^3$ is a group susceptible to reaction or removal under the particular conditions employed to introduce $R^4$, said $R^3$ group may itself be introduced at the final stage of the synthesis. Thus a phenol of formula (II), wherein $R^3$ is H, and $R^1$ and $R^2$ are as previously defined, which is obtainable for example by PD°-mediated deprotection of the O-allyl analogue, i.e. a compound of formula (II) wherein $R^3$ is allyl, and $R^1$ and $R^2$ are as previously defined, serves as the substrate for the subsequent reactions involved in introducing the various $R^4$ substituents. A final O-alkylation of the phenolic group is then necessary to furnish a compound of formula (I), wherein $R^1$, $R^2$, $R^3$ and $R^4$ as previously defined. This may be achieved under standard conditions using the appropriate alkyl chloride, bromide or sulphonate in the presence of a base such as anhydrous potassium carbonate, in a suitable solvent, e.g. 2-butanone, at the reflux temperature of the reaction mixture. Alternatively, the alkylation may be effected under typical Mitsunobu reaction conditions.

A compound of formula (II) may be prepared from a compound of formula (V):

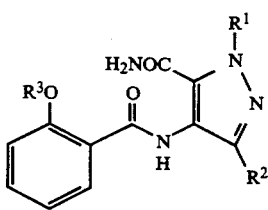

(V)

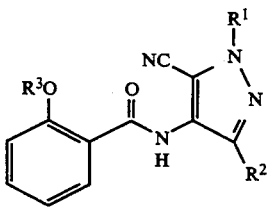

(VI)

wherein $R^1$, $R^2$ and $R^3$ are as previously defined, by the application of known cyclisation methods for pyrimidinone ring formation. Thus, for example, the cyclisation may be effected by the treatment of (V) with a base such as sodium hydroxide or potassium carbonate, optionally in the presence of hydrogen peroxide, in an ethanol-water medium at reflux temperature. Under these conditions the related nitrile of formula (VI), wherein $R^1$, $R^2$ and $R^3$ are as previously defined, may also be employed as the precursor to (IV).

In an alternative cyclisation procedure, compounds of the formula (II) may be obtained by treatment of (V) with polyphosphoric acid at about 140° C.

Compounds of formulae (V) and (VI) may be prepared from compounds of formulae (VII) and (VIII) respectively:

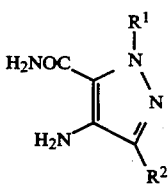

(VII)

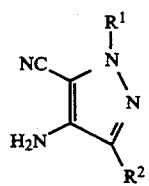

(VIII)

wherein $R^1$ and $R^2$ are as previously defined, by reaction with a compound of formula (IX):

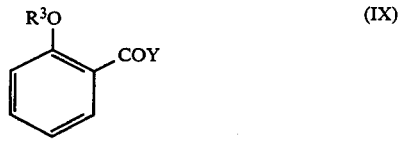

(IX)

wherein $R^3$ and Y are as previously defined.

The reaction is generally carried out using an excess of (IX) in the presence of an excess of a tertiary amine such as triethylamine to act as scavenger for the acid by-product (HY), optionally in the presence of a catalyst such as 4-dimethylaminopyridine, in an inert solvent such as dichloromethane at from about 0° C. to room temperature.

Compounds of formula (I) may be obtained more directly from a compound of formula (X):

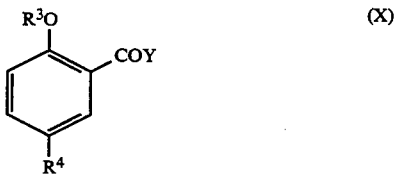

(X)

wherein $R^3$, $R^4$ and Y are as previously defined, when such acyl halides are readily accessible, by reaction with either (VII) or (VIII) and subsequent ring-closure of the product as described above. Clearly this alternative synthetic route will only be appropriate when $R^4$ is compatible with the reaction conditions obtaining in both steps, e.g. when $R^4$ is acetyl as illustrated by Example 17.

The aminopyrazoles of formulae (VII) and (VIII), the acyl halides of formulae (IX) and (X), and the intermediates employed for introduction of the various $R^4$ substituents into compounds of formula (II) to afford compounds of formula (I), when neither commercially available nor subsequently described, can be obtained by conventional synthetic procedures, in accordance with literature precedent, from readily accessible starting materials using appropriate reagents and reaction conditions.

Certain of the compounds of formula (I), wherein $R^9$ is as previously defined but not hydrogen, may be prepared directly from the corresponding 4-N-unsubstituted piperazine analogue, that is the precursor wherein $R^9$ is hydrogen, using appropriate standard synthetic procedures.

All of the above reactions are entirely conventional and the necessary reagents and conditions for their performance can readily be established by reference to standard text books and to the Examples provided hereafter. Alternatives and variations will also be evident to persons skilled in the art to enable all the compounds defined by formula (I) to be prepared.

The biological activities of the compounds of the present invention were determined by the following test methods.

Phosphodiesterase Activity

Compound affinities for cGMP and cAMP PDEs are assessed by determination of their $IC_{50}$ values (the concentration of inhibitor required for 50% inhibition of enzyme activity). The PDE enzymes are isolated from rabbit platelets and rat kidney, essentially by the method of W. J. Thompson et al. (Biochem., 1979, 10, 311). The calcium/calmodulin (Ca/CAM)-independent cGMP PDE and the cGMP-inhibited cAMP PDE enzymes are obtained from rabbit platelets whilst, of the four major PDE enzymes of the rat kidney, the Ca/CAM-dependent cGMP PDE (fraction I) is isolated. Assays are performed using a modification of the "batch" method of W. J. Thompson and M. M. Appleman (Biochem., 1979, 18, 5228). Results from these tests show that the compounds of the present invention are potent and selective inhibitors of both cGMP PDEs.

Platelet Anti-aggregatory Activity

This is assessed by the determination of a compound's ability to inhibit platelet aggregation in vitro induced by platelet activating factor (PAF), and to potentiate the platelet antiaggregatory action in vitro of activators of guanylate cyclase such as nitroprusside and EDRF. Washed platelets are prepared essentially by the method of J. F. Mustard et al. (Methods in Enzymol., 1989, 169, 3) and aggregation is determined using standard turbidimetric techniques as described by G. V. R. Born, (J. Physiol. (Lond), 1962, 162, 67P).

Antihypertensive Activity

This is assessed following intravenous or oral administration of a compound to spontaneously hypertensive rats. Blood pressure is recorded via a cannula implanted in the carotid artery of either conscious or anaesthetised animals.

For administration to man in the curative or prophylactic treatment of angina, hypertension or congestive heart failure, oral dosages of the compounds will generally be in the range of from 4–800 mg daily for an average adult patient (70 kg). Thus for a typical adult patient, individual tablets or capsules contain from 2–400 mg of active compound, in a suitable pharmaceutically acceptable vehicle or carrier, for administration in single or multiple doses, once or several times per day. Dosages for intravenous, buccal or sublingual administration will typically be within the range of from 1–400 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, the compounds of formula (I) can be administered alone, but will generally be administered in admixture with a pharmaceutical carrier selected with regard to the intended route of administration and standard pharmaceutical practice. For example, They may be administered orally, buccally or sublingually, in the form of tablets containing excipients such as starch or lactose, or in capsules or ovules either alone or in admixture with excipients, or in the form of elixirs or suspensions containing flavouring or colouring agents. The compounds may also be injected parenterally, for example intravenously, intramuscularly, subcutaneously or intracoronarily. For parenteral administration, they are best used in the form of a sterile aqueous solution which may contain other substances, for example salts, or monosaccharides such as mannitol or glucose, to make the solution isotonic with blood.

Thus the invention provides a pharmaceutical composition comprising a compound of formula (I), or a pharmaceutically acceptable salt thereof, together with a pharmaceutically acceptable diluent or carrier.

The invention also provides a compound of formula (I), or a pharmaceutically acceptable salt thereof, or a pharmaceutical composition containing either entity, for use in medicine.

The invention further provides the use of a compound of formula (I), or a pharmaceutically acceptable salt thereof, or a pharmaceutical composition containing either entity, for the manufacture of a medicament for the treatment of stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterised by disorders of gut motility, e.g. IBS.

In a further aspect, the invention provides a method of treating or preventing stable, unstable and variant (Prinzmetal) angina, hypertension, pulmonary hypertension, congestive heart failure, atherosclerosis, stroke, peripheral vascular disease, conditions of reduced blood vessel patency e.g. post-PTCA, chronic asthma, bronchitis, allergic asthma, allergic rhinitis, glaucoma, or diseases characterised by disorders of gut motility, e.g. IBS, in a mammal (including a human being), which comprises administering to said mammal a therapeutically effective amount of a compound of formula (I), or a pharmaceutically acceptable salt thereof, or a pharmaceutical composition containing either entity.

The invention also includes any novel intermediates of formulae (II), (III) and (IV) disclosed herein.

The syntheses of the compounds of the invention and of the intermediates for use therein are illustrated by the following Examples and Preparations. The purity of the compounds was routinely monitored by thin layer chromatography (TLC) using Merck Kieselgel 60 $F_{254}$ plates. $^1$H-Nuclear magnetic resonance spectra were recorded using either a Nicolet QE-300 or a Bruker AC-300 spectrometer and were in all cases consistent with the proposed structures.

EXAMPLE 1

5-(2-Ethoxy-5-piperidinoacetylphenyl)-1-methyl-3-n-propyl-1,6-dihydro-7H-pyrazolo[4,3-d]pyrimidin-7-one Piperidine (0.22 ml, 0.0022 mol) was added to a stirred suspension of 5-(5-bromoacetyl-2-ethoxyphenyl)-1-methyl-3-n-propyl-1,6-dihydro-7H-pyrazolo[4,3-d]pyrimidin-7-one (Preparation 8, 0.95 g, 0.0022 mol) and anhydrous potassium carbonate (0.6 g, 0.0044 mol) in acetonitrile (50 ml) at room temperature. After 18 hours the mixture was evaporated under vacuum, the residue dissolved in water (50 ml) and the solution extracted with ethyl acetate (3×30 ml). The organic extracts were combined, washed with brine (3×20 ml), dried ($Na_2SO_4$) and evaporated under vacuum. The resulting yellow solid was chromatographed on silica gel (12g), using a methanol in dichloromethane elution gradient (0–2% methanol), to give an off-white solid. Crystallisation from ethyl acetate-hexane gave the title compound as an off-white powder (0.27 g, 28%), m.p. 149°–151° C. Found: C,66.13; H,6.90; N,15.95. $C_{24}H_{31}N_5O_5$ requires C,65,88; H,7.14; N,16.01%.

EXAMPLES 2–8

The following Examples were prepared by the procedure of Example 1 using the appropriate amine.

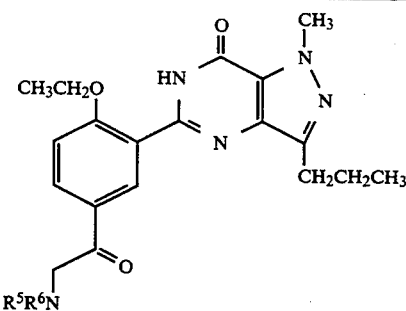

| Example | NR⁵R⁶ | % yield | m.p. (°C.) | Analysis % (theoretical in brackets) C | H | N |
|---|---|---|---|---|---|---|
| 2 | N(CH₂CH₃)₂ | 4 | 120–121 | 65.21 (64.92 | 7.31 7.34 | 16.37 16.46) |
| 3 | N⌒NCOCH₃ | 23 | 183–185 | 62.48 (62.48 | 6.62 6.71 | 17.32 17.49) |
| 4 | N⌒O | 29 | 159–160 | 63.20 (62.85 | 6.58 6.65 | 15.87 15.94) |
| 5 | CH₃ imidazolyl | 21 | 202–204 | 61.84 (62.28 | 6.12 6.14 | 18.68 18.95)ᵃ |
| 6 | N⌒NH | 39 | 142–143 | 62.83 (63.00 | 7.09 6.90 | 18.90 19.16) |
| 7 | N⌒NCH₂CH₂OH | 36 | 135–136 | 62.46 (62.22 | 6.91 7.10 | 17.36 17.41) |
| 8 | N⌒—OH | 40 | 151–152 | 63.64 (63.56 | 6.80 6.89 | 15.63 15.44) |

ᵃ0.50 H₂O

EXAMPLE 9

5-{2-Ethoxy-5-[1-hydroxy-2-(1-piperazinyl)ethyl]-phenyl}-1-methyl-3-n-propyl-1,6-dihydro-7H-pyrazolo[4,3-d]pyrimidin-7-one Sodium borohydride (0.01 g, 0.0027 mol) was added to a stirred suspension of 5-([2-ethoxy-5-(1-piperazinylacetyl)phenyl-1-methyl-3-n-propyl-1,6-dihydro-7H-pyrazolo[4,3-d]pyrimidin-7-one (0.12 g, 0.0027 mol) in ethanol (10 ml) and the resulting solution stirred at room temperature for 18 hours. The solvent was removed by evaporation under vacuum, the residue suspended in saturated aqueous sodium carbonate solution (50 ml) and this mixture extracted with dichloromethane (3×20 ml). The organic extracts were combined, dried (Na₂SO₄) and evaporated under vacuum to give an oil. Trituration with ether gave a white solid, crystallisation of which from ethyl acetate-hexane gave the title compound as a white powder (0.050 g, 42%), m.p. 130°–140° C. Found: C,62.55; H,7.44; N,18.79. C₂₃H₃₂N₆O₃ requires C,62.71; H,7.32; N,19.08%.

EXAMPLES 10–13

The following Examples were prepared by the procedure of Example 9 using the appropriate ketones (Examples 3, 4, 5 and 1 respectively).

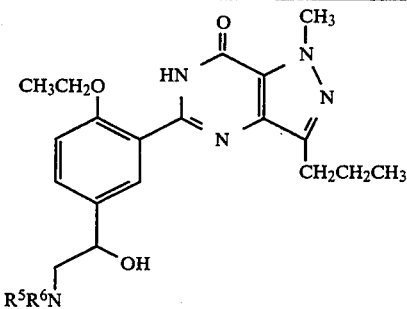

| Example | NR⁵R⁶ | % yield | m.p. (°C.) | C | H | N |
|---|---|---|---|---|---|---|
| 10 | N∕―∖NCOCH₃ | 37 | 139–141 | 61.92 (62.22 | 7.01 7.10 | 17.08 17.42) |
| 11 | N∕―∖O | 69 | 125–127 | 62.23 (62.56 | 7.10 7.08 | 15.53 15.86) |
| 12 | imidazole-CH₃ | 77 | 221–222 | 63.68 (63.29 | 6.39 6.47 | 19.17 19.25) |
| 13 | piperidine | 97 | 117–118 | 65.51 (65.58 | 7.57 7.57 | 15.84 15.93) |

EXAMPLE 14

1-Methyl-5-(5-morpholinoacetyl-2-n-propoxyphenyl)-3-n-propyl-1,6-dihydro-7H-pyrazolo[4,3-d]pyrimidin-7-one This compound was prepared from morpholine and 5-(5-bromoacetyl-2-n-propoxyphenyl)-1-methyl-3-n-propyl-1,6-dihydro-7H-pyrazolo[4,3-d]pyrimidin-7-one (Preparation 11), following the procedure of Example 1, and was obtained as white crystals (47%), m.p. 128°–129° C. Found: C,63.62; H,7.07; N,15.53. $C_{24}H_{31}N_5O_4$ requires C,63.56; H,6.89; N,15.44%.

EXAMPLE 15

1-Methyl-5-[5-(4-methyl-1-piperazinylacetyl)-2-n-propoxyphenyl[-3-n-propyl-1,6-dihydro-7H-pyrazolo[4,3-d]pyrimidin-7-one This compound was prepared from 4-methylpiperazine and 5-(5-bromoacetyl-2-n-propoxyphenyl)-1-methyl-3-n-propyl-1,6-dihydro-7H-pyrazolo[4,3-d]pyrimidin-7-one (Preparation 11), following the procedure of Example 1, and was obtained as a white solid (27%), m.p. 124°–125° C. Found: C,63.96; H,7.19; N,17.80. $C_{25}H_{34}N_6O_3$ requires C,64.36; H,7.34; N,18.01%.

EXAMPLE 16

5-[5-(1-Hydroxy-2-morpholinoethyl)-2-n-propoxyphenyl]-1-methyl-3-n-propyl-1,6-dihydro-7H-pyrazolo[4,3-d]pyrimidin-7-one This compound was prepared from 1-methyl-5-(5-morpholinoacetyl-2-n-propoxyphenyl)-3-n-propyl-1,6-dihydro-7H-pyrazolo[4,3-d]pyrimidin-7-one, following the procedure of Example 9, and was obtained as a white solid (28%), m.p. 104°–105° C. Found: C,62.90; H,7.50; N,15,48. $C_{24}H_{33}N_5O_4$ requires C,63.28; H,7.30; N,15,37%.

EXAMPLE 17

5-(5-Acetyl-2-ethoxyphenyl)-1-methyl-3-n-propyl-1,6-dihydro-7H-pyrazolo[4,3-d]pyrimidin-7-one The title compound was prepared from 4-(5-acetyl-2-ethoxybenzamido)-1-methyl-3-n-propylpyrazole-5-carboxamide (Preparation 15), following the procedure of Preparation 7, and was obtained as a white solid (77%), m.p. 196°–198° C. Found: C,64.35; H,6.16; H,15.85. $C_{19}H_{22}N_4O_3$ requires C,64.39; H,6.26; N,15.81%.

EXAMPLE 18

5-(5-Bromo-2-n-propoxyphenyl)-1-methyl-3-n-propyl-1,6-dihydro-7H-pyrazolo[4,3-d]pyrimidin-7-one N-Bromosuccinimide (2,6g, 0.016 mol) in dimethylformamide (40 ml) was added dropwise to a stirred solution of 5-(2-n-propoxyphenyl)-1-methyl-3-n-propyl- 1,6-dihydro-7H-pyrazolo[4,3-d]pyrimidin-7-one (Preparation 10, 4.0 g, 0.010 mol) in dimethylformamide (40 ml) at room temperature. After 7 hours the solvent was removed by evaporation under vacuum, the residue suspended in saturated aqueous sodium carbonate solution, and the resulting solution extracted with ethyl acetate (3×50 ml). The organic extracts were combined, dried ($Na_2SO_4$) and evaporated under vacuum. Trituration of the residue with ether, followed by crystallisation from ethyl acetate-hexane, gave the title compound as white crystals (3.39 g, 68%), m.p. 117°–118° C. Found: C,53.15; H,5.03; N,13,78. $C_{18}H_{21}BrN_4O_2$ requires C,53,34; N,5.22; N,13.82%.

EXAMPLE 19

(E)-3-(1-Methyl-7-oxo-3-n-propyl-1,6-dihydro-7H-pyrazolo[4,3-d]pyrimidin-5-yl)-4-n-propoxycinnamic acid t-butyl ester To a solution of 5-(5-bromo-2-n-propoxyphenyl)-1-methyl-3-n-propyl-1,6-dihydro-7H-pyrazolo[4,3-d]pyrimidin-7-one (1.0 g, 0.0025 mol) and triethylamine (0.38 g, 0.0038 mol) in acetonitrile (2 ml), was added palladium(II) acetate (0.03 g, 0.00013 mol), tri-o-tolylphosphine (0.076 g, 0.00025 mol) and t-butyl acrylate (0.48 g, 0.00038 mol). The mixture was heated under reflux for 4 hours, then cooled and evaporated under vacuum. The residue was suspended in water (30 ml) and extraction with dichloromethane (3×20 ml) effected. The organic extracts were combined, dried ($Na_2SO_4$) and evaporated under vacuum to give a yellow-green solid. Chromatography on silica gel (12 g), using a methanol in dichloromethane elution gradient (0–2% methanol), followed by crystallisation from ethyl acetate-hexane gave the title compound as a white solid (0.65 g, 58%), m.p. 167°–168° C. Found: C,66.47; H,7.00; N,12.31. $C_{25}H_{32}N_4O_4$ requires C,66.35; H,7.13; N,12.38%.

EXAMPLE 20

(E)-3-(1-Methyl-7-oxo-3-n-propyl-1,6-dihydro-7H-pyrazolo[4,3-d]pyrimidin-5-yl)-4-n-propoxycinnamic acid 2N Aqueous sodium hydroxide solution (2.28 ml, 0.0046 mol) was added to a solution of (E)-3-(1-methyl-7-oxo-3-n-propyl-1,6-dihydro-7H-pyrazolo[4,3-d]pyrimidin-5-yl)-4-n-propoxycinnamic acid t-butyl ester (0.40 g, 0.00088 mol) in methanol (2.3 ml) and the mixture was heated under reflux for 18 hours. The methanol was removed by evaporation under vacuum, the residue dissolved in water (25 ml), and the solution extracted with ethyl acetate (4×15 ml). The aqueous layer was separated, acidified to pH 1 with hydrochloric acid, and then extracted with a mixture of methanol and ethyl acetate (3:97, 4×20 ml). The organic extracts were combined, dried ($Na_2SO_4$) and evaporated under vacuum, then the residue crystallised from ethyl acetate to give the title compound as a white solid (0.27 g, 77%), m.p. 229°–230° C. Found: C,63.64; H,5.98; N,14.14. $C_{21}H_{25}N_4O_4$ requires C,63.46; H,6.34; N,14.10%.

EXAMPLE 21

5-(5-Bromo-2-ethoxyphenyl)-1-methyl-3-n-propyl-1,6-dihydro-7H-pyrazolo[4,3-d]pyrimidin-7-one Bromine (0.93 g, 0.0058 mol) was added dropwise to a stirred solution of 5-(2-ethoxyphenyl)-1-methyl-3-n-propyl-1,6-dihydro-7H-pyrazolo[4,3-d]pyrimidin-7-one (Preparation 7, 1.1 g, 0.00352 mol) in glacial acetic acid (20 ml). The mixture was stirred at 100° C. for 6.5 hours and the solvent was then removed by evaporation under vacuum. The residue was dissolved in a 9:1 mixture of methanol in dichloromethane (50 ml), and the solution washed with saturated aqueous sodium bicarbonate solution (50 ml), water (50 ml) and saturated brine (50 ml), then dried ($MgSO_4$) and evaporated under vacuum. The residue was chromatographed on silica gel (15 g) eluting with a mixture of methanol and dichloromethane (1:99) to give, after crystallisation from acetonitrile, the title compound (0.62 g, 45%), m.p. 157°–159° C. Found: C,52.41; H,5.25; N,14.01. $C_{17}H_{19}BrN_4O_2$ requires C,52.18; H,4.89; N,14.32%.

EXAMPLE 22

(E)-4-Ethoxy-3-(1-methyl-7-oxo-3-n-propyl-1,6-dihydro-7H-pyrazolo[4,3-d]pyrimidin-5-yl)cinnamic acid t-butyl ester The title compound was prepared from 5-(5-bromo-2-ethoxyphenyl)-1-methyl-3-n-propyl-1,6-dihydro-7H-pyrazolo[4,3-d]pyrimidin-7-one following the procedure of Example 19 and was obtained as a white crystalline solid (31%), m.p. 179°–180° C. Found: C,65.83; H,6.90; N,12.75. $C_{24}H_{30}N_4O_4$ requires C,65.89; H,6.68; N,12.81%.

EXAMPLE 23

(E)-4-Ethoxy-3-(1-methyl-7-oxo-3-n-propyl-1,6-dihydro-7H-pyrazolo[4,3-d]pyrimidin-5-yl)cinnamic acid The title compound was prepared from (E)-4-ethoxy-3-(1-methyl-7-oxo-3-n-propyl-1,6-dihydro-7H-pyrazolo[4,3-d]pyrimidin-5-yl)cinnamic acid t-butyl ester following the procedure of Example 20 and was obtained as white crystals (66%), m.p. 234°–236° C. Found: C,63.01; H,5.59; N,14.62. $C_{20}H_{22}N_4O_4$ requires C,62.82; H,5.80; N,14.65%.

EXAMPLE 24

3-[4-Ethoxy-3-(1-methyl-7-oxo-3-n-propyl-1,6-dihydro-7H-pyrazolo[4,3-d]pyrimidin-5-yl)phenyl]propanoic acid A solution of (E)-4-Ethoxy-3-(1-methyl-7-oxo-3-n-propyl-1,6-dihydro-7H-pyrazolo[4,3-d]pyrimidin-5-yl)cinnamic acid (0.426 g, 0.0011 mol) in a mixture of methanol (28.5 ml), ethyl acetate (100 ml) and water (1.5 ml), was stirred with 5% palladium on charcoal catalyst (0.05 g) under a hydrogen atmosphere at room temperature and pressure for 3 hours. The catalyst was removed by filtration and the solvent removed by evaporation under vacuum. Crystallisation of the residue from ethyl acetate-hexane gave the title compound as beige crystals (0.23 g, 54%), m.p. 165°–167° C. Found: C,62.25; H,6.17; N,14.09. $C_{20}H_{24}N_4O_4$ requires C,62.39; H,6.33; N,14.41%

EXAMPLE 25

(E)-4-Ethoxy-3-(1-methyl-7-oxo-3-n-propyl-1,6-dihydro-7H-pyrazolo[4,3-d]pyrimidin-5-yl)cinnamic acid dimethylamide The title compound was prepared from N,N-dimethylacrylamide and 5-(5-bromo-2-ethoxyphenyl)-1-methyl-3-n-propyl-1,6-dihydro-7H-pyrazolo[4,3-d]pyrimidin-7-one following the procedure of Example 19 and was obtained, following crystallisation from ethyl acetate-hexane, as colourless crystals (38%), m.p.

219°–221° C. Found: C,64.15; H,6.46; N,16.96. C$_{22}$H$_{27}$N$_5$O$_3$ requires C,64.53; H,6.65; N,17.10%.

EXAMPLE 26

3-[4-Ethoxy-3-(1-methyl-7-oxo-3-n-propyl-1,6-dihydro-7H-pyrazolo[4,3-d]pyrimidin-5-yl)phenyl]propanoic acid dimethylamide The title compound was prepared from (E)-4-ethoxy-3-(1-methyl-7-oxo-3-n-propyl-1,6-dihydro-7H-pyrazolo[4,3-d]pyrimidin-5-yl)cinnamic acid dimethylamide following the procedure of Example 24 and, after crystallisation from ethyl acetate-hexane, was obtained as colourless crystals (74%), m.p. 155°–157° C. Found: C,64.09; H,7.04; N,16.71. C$_{22}$H$_{29}$N$_5$O$_3$ requires C,64.21; H,7.10; N,17.02%.

EXAMPLE 27

(E)-4-Ethoxy-3-(1-methyl-7-oxo-3-n-propyl-1,6-dihydro-7H-pyrazolo[4,3-d]pyrimidin-5-yl)cinnamonitrile The title compound was prepared from acrylonitrile and 5-(5-bromo-2-ethoxyphenyl)-1-methyl-3-n-propyl-1,6-dihydro-7H-pyrazolo[4,3-d]pyrimidin-7-one following the procedure of Example 19 and was obtained as off-white crystals (33%). Found: C,65.99; H,5.52; N,19.07. C$_{20}$H$_{21}$N$_5$O$_2$ requires C,66.10; H,5.82; N,19.27%.

EXAMPLE 28

5-[5-(3-Aminopropyl)-2-ethoxyphenyl]-1-methyl-3-n-propyl-1,6-dihydro-7H-pyrazolo[4,3-d]pyrimidin-7-one A solution of (E)-4-ethoxy-3-(1-methyl-7-oxo-3-n-propyl-1,6-dihydro-7H-pyrazolo[4,3-d]pyrimidin-5-yl)cinnamonitrile (0.25 g, 0.00064 mol) in glacial acetic acid (25 ml) was stirred with Raney nickel catalyst (25 mg) under hydrogen at room temperature and at 50 p.s.i. for 3 hours. The resulting mixture was filtered and the filtrate evaporated under vacuum. The residue was partitioned between saturated aqueous sodium carbonate solution (50 ml) and dichloromethane (30 ml), the layers separated and the aqueous phase further extracted with dichloromethane (2×30 ml). The organic solutions were combined, dried (Na$_2$SO$_4$) and evaporated under vacuum to give a brown solid, crystallisation of which from hexane-ethyl acetate gave the title compound as fawn crystals (96 mg, 38%), m.p. 115°–117° C. Found C,65.29; H,7.35; N,18.66. C$_{20}$H$_{27}$N$_5$O$_2$ requires C,65.02; H,7.37; N,18.96%.

EXAMPLE 29

4-Ethoxy-3-(1-methyl-7-oxo-3-n-propyl-1,6-dihydro-7H-pyrazolo[4,3-d]pyrimidin-5-yl)benzoic acid n-Butyllithium (2.5M solution in hexane, 1.53 ml, 0.0038 mol) was added dropwise to a stirred solution of 5-(5-bromo-2-ethoxyphenyl)-1-methyl-3-n-propyl-1,6-dihydro-7H-pyrazolo[4,3-d]pyrimidin-7-one (0.60 g, 0.00074 mol) in dry tetrahydrofuran (25 ml) at −78° C. under a dry nitrogen atmosphere. After 0.3 hour at −78° C., the solution was allowed to warm to −40° C. and carbon dioxide gas was bubbled through the solution. The resulting solution was allowed to warm to room temperature and then poured into water; acidification to pH 3 with 2N hydrochloric acid and extraction with a 9:1 mixture of dichloromethane and methanol (4×50 ml) were then effected. The organic extracts were combined, dried (MgSO$_4$) and evaporated under vacuum to give a colourless solid. Chromatography of this solid on silica gel (20 g), using a methanol in dichloromethane elution gradient (2–5% methanol), gave a solid which was dissolved in a 9:1 mixture of dichloromethane and methanol (50 ml); this solution was then washed with saturated aqueous sodium carbonate solution (50 ml), dried (MgSO$_4$) and evaporated under vacuum to give the title compound as a white powder (0.144 g, 26%), m.p. 285°–288° C. Found: C,60.74; H,5.72; N,15.61. C$_{18}$H$_{20}$N$_4$O$_4$ requires C,60.66; H,5.66; N,15.72%.

EXAMPLE 30

5-[2-Ethoxy-5-(4-methylpiperazinylcarbonyl)phenyl]-1-methyl-3-n-propyl-1,6-dihydro-7H-pyrazolo[4,3-d]pyrimidin-7-one A solution of 4-ethoxy-3-(1-methyl-7-oxo-3-n-propyl-1,6-dihydro-7H-pyrazolo[4,3-d]pyrimidin-5-yl)benzoic acid (0.095 g, 0.00027 mol), 1-methylpiperazine (0.265 g, 0.00265 mol), 1-(3-dimethylaminopropyl)-3-ethylcarbodiimide hydrochloride (0.077 g, 0.0004 mol) and 1-hydroxybenzotriazole (0.054 g, 0.0004 mol) in dichloromethane (25 ml) was stirred at room temperature for 18 hours. The reaction solution was washed with water (25 ml), dried (MgSO$_4$) and evaporated under vacuum, and then the resulting residue crystallised from ethyl acetate-hexane to give the title compound as colourless crystals (0.03 g, 25%), m.p. 196°–197° C. Found: C,63.12; H,6.81; H,18.96. C$_{23}$H$_{30}$N$_6$O$_3$ requires C,62.99; H,6.90; N,19.16%.

EXAMPLE 31

5-[2-Ethoxy-5-(1-imidazolyl)phenyl]-1-methyl-3-n-propyl-1,6-dihydro-7H-pyrazolo[4,3-d]pyrimidin-7-one A solution of 5-(5-bromo-2-ethoxyphenyl)-1-methyl-3-n-propyl-1,6-dihydro-7H-pyrazolo[4,3-d]pyrimidin-7-one (0.20 g, 0.0051 mol), imidazole (0.172 g, 0.0025 mol), anhydrous potassium carbonate (0.077 g, 0.00056 mol), copper bronze (0.036 g, 0.00057 mol) and iodine (0.015 g, 0.00012 mol) in dimethylformamide (10 ml) was heated under reflux under nitrogen for 4.5 hours, cooled and poured into water (50 ml). This mixture was extracted with a 9:1 mixture of dichloromethane and methanol (6×50 ml) and the extracts combined, dried (MgSO$_4$) and evaporated under vacuum to give a pale brown oil. The oil was chromatographed on silica gel (20 g), eluting with a mixture of dichloromethane, methanol and triethylamine (97.8:20:0.2), to give a yellow solid, crystallisation of which from ethyl acetate-hexane gave the title compound as a cream solid (0.073 g, 38%), m.p. 193°–194° C. Found: C,63.61; H,5.97; N,22.03. C$_{20}$H$_{22}$N$_6$O$_2$ requires C,63.48; H,5.86; N,22.21%.

EXAMPLE 32

5-[2-Ethoxy-5-(1-methyl-2-imidazolyl)phenyl]-1-methyl-3-n-propyl-1,6-dihydro-7H-pyrazolo[4,3-d]pyrimidin-7-one n-Butyllithium (1.6M solution in hexane, 9.6 ml, 0.0153 mol) was added to a stirred solution of 1-methylimidazole (0.628 g, 0.0077 mol) in dry tetrahydrofuran (10 ml) at −78° C., and the resulting solution stirred for 0.25 hours. A solution of anhydrous zinc chloride (2.08 g, 0.0153 mol) in dry tetrahydrofuran (15 ml) was added, the mixture allowed to warm to room temperature, then 5-(5-bromo-2-ethoxyphenyl)-1-methyl-3-n-propyl-1,6-dihydro-7H-pyrazolo[4,3-d]pyrimidin-7-one (1.0 g, 0.0026 mol) and tetrakis(triphenylphosphine)palladium(0) (0.036 g, 0.031 mmol) were added and the mixture heated under reflux for 18 hours. A further quantity of anhydrous zinc chloride (2.08 g, 0.0153 mol) was added and the resulting mixture heated under reflux for a further 60 hours, then cooled; methanol (2 ml) was added and the solvent removed by evaporation under vacuum. The residue was heated with a solution of disodium ethylenediaminetetraacetic acid dihydrate (23.0 g, 0.0618 mol) in water (100 ml) to 100° C. for 0.2 hour, then the resulting solution basified to pH 8 with saturated aqueous sodium carbonate solution and extracted with dichloromethane (6×100 ml). The organic extracts were combined, dried ($Na_2SO_4$) and evaporated under vacuum to give a yellow solid, purification of which by chromatography on silica gel (13 g), using a methanol-dichloromethane elution gradient (0–3% methanol), followed by crystallisation from ethyl acetate, gave the title compound as an off-white solid (0.542 g, 53%), m.p. 199°–202° C. Found: C,64.45; H,6.27; N,21.56. $C_{21}H_{24}N_6O_2$ requires C,64.27; H,6.16; N,21.42%.

EXAMPLE 33

5-[2-Ethoxy-5-(2-pyridyl)phenyl-1-methyl-3-n-propyl-1,6-dihydro-7H-pyrazolo[4,3-d]pyrimidin-7-one The title compound was prepared from 2-bromopyridine and 5-(5-bromo-2-ethoxyphenyl)-1-methyl-3-n-propyl-1,6-dihydro-7H-pyrazolo[4,3-d]pyrimidin-7-one, following the procedure described in Example 32, and was obtained as an off-white solid (33%), m.p. 216°–218° C. Found: C,67.71; H,5.81; N,17.63. $C_{22}H_{23}N_5O_2$ requires C,67.85; H,5.95; N,17.98%.

EXAMPLE 34

1-Methyl-5-(5-morpholinomethyl-2-n-propoxyphenyl)-3-n-propyl-1,6-dihydro-7H-pyrazolo[4,3-d]pyrimidin-7-one A solution of 5-(5-chloromethyl-2-n-propoxyphenyl)-1-methyl-3-n-propyl-1,6-dihydro-7H-pyrazolo[4,3-d]pyrimidin-7-one (Preparation 16, 0.60 g, 0.0016 mol) in 2-butanone (10 ml) was added dropwise to a stirred solution of morpholine (0.42 g, 0.0048 mol) in 2-butanone (40 ml) at 0° C. The solution was then heated under reflux for 16 hours, cooled and evaporated under vacuum. The residue was suspended in water (50 ml) and the suspension extracted with ethyl acetate (3×20 ml). The organic extracts were combined, washed with brine (2×30 ml), dried ($Na_2SO_4$) and evaporated under vacuum. The residue was chromatographed on silica gel (12 g), using an elution gradient of methanol in dichloromethane (0–2% methanol), to give an oil which solidified on trituration with hexane. Crystallisation from ethyl acetate-hexane gave the title compound as a colourless solid (0.36 g, 53%), m.p. 106°–107° C. Found: C,64.76; H,7.34; N,16.36. $C_{23}H_{31}N_5O_3$ requires C,64.92; H,7.34; N,16.46%.

EXAMPLE 35

1-Methyl-5-[5-(4-methyl-1-piperazinylmethyl)-2-n-propoxyphenyl]-3-n-propyl-1,6-dihydro-7H-pyrazolo[4,3-d]pyrimidin-7-one The title compound was prepared from 5-(5-chloromethyl-2-n-propoxyphenyl)-1-methyl-3-n-propyl-1,6-dihydro-7H-pyrazolo[4,3-d]pyrimidin-7-one and 1-methylpiperazine, following the procedure of Example 34, and was obtained as a colourless solid (36%), m.p. 149°–150° C. Found: C,65.68; H,7.83; N,19.10. $C_{24}H_{34}N_6O_2$ requires C,65.73; H,7.81; N,19.16%.

EXAMPLE 36

1-Methyl-5-(5-methyl-2-n-propoxyphenyl)-3-n-propyl-1,6-dihydro-7H-pyrazolo[4,3-d]pyrimidin-7-one A solution of 5-(5-chloromethyl-2-n-propoxyphenyl)-1-methyl-3-n-propyl-1,6-dihydro-7H-pyrazolo[4,3-d]pyrimidin-7-one (0.5 g, 0.0013 mol) in ethyl acetate (50 ml) was stirred with 10% palladium on charcoal catalyst under a hydrogen atmosphere at 50 p.s.i. and room temperature. After 1 hour, the mixture was filtered and the filtrate evaporated under vacuum to give a pale green solid. Chromatography on silica gel (4 g) using a methanol in dichloromethane elution gradient gave a white solid, crystallisation of which from hexane-ethyl acetate gave the title compound as colourless needles (0.12 g, 26%), m.p. 115°–116° C. Found: C,66.66; N,7.12; N,16.55. $C_{19}H_{24}N_4O_2$ requires C,67.04; H,7.11; N,16.46%.

EXAMPLE 37

5-(5-Hydroxymethyl-2-n-propoxyphenyl)-1-methyl-3-n-propyl-1,6-dihydro-7H-pyrazolo[4,3-d]pyrimidin-7-one To a solution of 5-(5-chloromethyl-2-n-propoxyphenyl)-1-methyl-3-n-propyl-1,6-dihydro-7H-pyrazolo[4,3-d]pyrimidin-7-one (0.5 g, 0.0013 mol) in dimethyl sulphoxide (10 ml) was added sodium hydroxide (0.26 g, 0.0065 mol) and ethylene glycol (0.41 g, 0.0065 mol). The reaction mixture was heated at 100° C. for 6 hours, allowed to cool and poured into water (50 ml), then the aqueous mixture extracted with ethyl acetate (3×30 ml). The combined extracts were filtered, dried ($Na_2SO_4$) and evaporated under vacuum to provide an oil which was purified by chromatography on silica gel (6 g), using a methanol in dichloromethane elution gradient (0–3% methanol). The solid product was crystallised from hexane-ethyl acetate to afford the title compound as a white solid (2%), m.p. 174°–175° C. Found: C,63.97; H,6.66; N,15.57. $C_{19}H_{24}N_4O_3$ requires C,64.03; H,6.79; N,15.72%.

EXAMPLE 38

5-(5-Ethoxymethyl-2-n-propoxyphenyl)-1-methyl-3-n-propyl-1,6-dihydro-7H-pyrazolo[4,3-d]pyrimidin-7-one Sodium (0.15 g, 0.0013 mol) was added portionwise to ethanol (40 ml) over 1 hour. 5-(5-Chloromethyl-2-n-propoxyphenyl)-1-methyl-3-n-propyl-1,6-dihydro-7H-pyrazolo[4,3-d]pyrimidin-7-one (0.5 g, 0.0013 mol) was then added to the solution and, after 3 days at room temperature, the solvent was removed by evaporation under vacuum. The residual solid was suspended in water (50 ml) and the suspension extracted with ethyl acetate (3×30 ml). The extracts were then combined, dried ($Na_2SO_4$) and evaporated under vacuum to give a green solid. Chromatography on silica gel (6 g) using a methanol in dichloromethane elution gradient gave, after crystallisation of the required product from a hexane-ethyl acetate mixture, the title compound as a white solid (0.2 g, 39%) m.p. 89°–90° C. Found: C,65.87; H,7.57; N,14.66. $C_{21}H_{28}N_4O_3$ requires C,65.60; H,7.34; N,14.57%.

EXAMPLE 39

5-[5-(2-Hydroxyethoxymethyl)-2-n-propoxyphenyl]-1-methyl-3-n-propyl-1,6-dihydro-7H-pyrazolo[4,3-d]pyrimidin-7-one This compound was prepared from 5-(5-chloromethyl-2-n-propoxyphenyl)-1-methyl-3-n-propyl-1,6-dihydro-7H-pyrazolo[4,3-d]pyrimidin-7-one and ethylene glycol following the procedure of Example 38 and was obtained as a white solid (45%), m.p. 101°–102° C. Found: C,63.13; H,6.88; N,13.98. $C_{21}H_{28}N_4O_4$ requires C,62.98; H,7.05; N,13.99%.

EXAMPLE 40

1-Methyl-5-[5-(2-morpholinoethoxymethyl)-2-n-propoxyphenyl]-3-n-propyl-1,6-dihydro-7H-pyrazolo[4,3-d]pyrimidin-7-one (a) Methanesulphonyl chloride (0.56 g, 0.0049 mol) was added to a stirred solution of 5-[5-(2-hydroxyethoxymethyl)-2-n-propoxyphenyl]-1-methyl-3-n-propyl-1,6-dihydro-7H-pyrazolo[4,3-d]pyrimidin-7-one (1.8 g, 0.0045 mol) in pyridine (25 ml) at 0° C. After 18 hours at room temperature, the solvent was removed by evaporation under vacuum and the residue partitioned between 2N hydrochloric acid (30 ml) and dichloromethane (30 ml). The aqueous layer was separated and extracted with dichloromethane (2×30 ml), then the organic solutions combined, dried ($Na_2SO_4$) and evaporated under vacuum to give a brown oil. Chromatography on silica gel (12 g) using a methanol in dichloromethane elution gradient (0–3% methanol) gave an oil, trituration of which with hexane, followed by crystallisation from hexane-ethyl acetate, gave the required mesylate as white crystals (0.19 g, 9%), m.p. 74°–76° C. Found: C,55.71; H,6.25; H,11.69. $C_{22}H_{30}N_4O_6S$ requires C,55.21; H,6.32; N,11.71%.

(b) Morpholine (0.19 g, 0.0021 mol) was added to a solution of the above mesylate, namely 5-[5-(2-methanesulphonyloxyethoxymethyl)-2-n-propoxyphenyl]-1-methyl-3-n-propyl-1,6-dihydro-7H-pyrazolo[4,3-d]pyrimidin-7-one, (0.20 g, 0.00042 mol) in acetonitrile (25 ml) and the stirred mixture was heated under reflux for 18 hours. The solvent was removed by evaporation under vacuum, the residue dissolved in saturated aqueous sodium carbonate solution and the solution extracted with ethyl acetate (3×20 ml). The extracts were combined, dried ($Na_2SO_4$) and evaporated under vacuum, and the residue was chromatographed on silica gel (4 g) using an elution gradient of methanol in dichloromethane (0–2% methanol). Evaporation under vacuum of the appropriate fractions, followed by crystallisation from hexane, gave the title compound as white crystals (0.098 g, 48%), m.p. 65°–66° C. Found: C,64.17; H,7.69; N,14.96; $C_{25}H_{35}N_5O_5$ requires C,63.94; H,7.51; N,14.91%.

EXAMPLE 41

5-(2-Ethoxy-5-methanesulphonamidophenyl)-1-methyl-3-n-propyl-1,6-dihydro-7H-pyrazolo[4,3-d]pyrimidin-7-one Methanesulphonyl chloride (0.157 g, 0.00137 mol) was added to a stirred solution of 5-(5-amino-2-ethoxyphenyl)-1-methyl-3-n-propyl-1,6-dihydro-7H-pyrazolo[4,3-d]pyrimidin-7-one (0.45 g, 0.00137 mol) in dry pyridine (30 ml) at 0° C. The mixture was stirred for 18 hours at room temperature and then evaporated under vacuum. The residue was suspended in saturated aqueous sodium bicarbonate solution (50 ml) and the mixture extracted with dichloromethane (2×30 ml). The organic extracts were combined, washed with brine (2×30 ml), dried ($Na_2SO_4$) and evaporated under vacuum. The residue was triturated with ether, chromatographed on silica gel (12 g), eluting with a 98.5:1.5 mixture of dichloromethane and methanol, and the required product crystallised from ethyl acetate-hexane to give the title compound as a white powder (0.32 g, 58%), m.p. 205°–206° C. Found: C,53.63; H,5.66; N,17.24. $C_{18}H_{23}N_5O_4S$ requires C,53.32; H,5.72; N,17.27%.

EXAMPLE 42

5-[2-Ethoxy-5-(3-morpholinopropylsulphonamido)-phenyl]-1-methyl-3-n-propyl-1,6-dihydro-7H-pyrazolo[4,3-d]pyrimidin-7-one The title compound was prepared from 5-(5-amino-2-ethoxyphenyl)-1-methyl-3-n-propyl-1,6-dihydro-7H-pyrazolo[4,3-d]pyrimidin-7-one and 3-morpholinopropylsulphonyl chloride, following the procedure of Example 41, and was obtained as brown crystals (14%), m.p. 157°–159° C. Found: C,55.42; H,6.53; N,16.01. $C_{24}H_{34}N_6O_5S$ requires C,55.58; H,6.61; N,16.21%.

EXAMPLE 43

5-[2-Ethoxy-5-(4-methyl-1-piperazinyl)sulphonamidophenyl]-1-methyl-3-n-propyl-1,6-dihydro-7H-pyrazolo[4,3-d]pyrimidin-7-one The title compound was prepared from 4-methyl-1-piperazinylsulphonyl chloride and 5-(5-amino-2-ethoxyphenyl)-1-methyl-3-n-propyl-1,6-dihydro-7H-pyrazolo[4,3-d]pyrimidin-7-one, following the procedure of Example 41, and was obtained as an orange powder (13%), m.p. 152°–153° C. Found: C,54.32; H,6.38; N,19.88. $C_{22}H_{31}N_7O_4S$ requires C,53.97; H,6.38; N,20.03%.

EXAMPLE 44

5-[5-(4-Benzyl-1-piperazinylsulphonamidophenyl)-2-ethoxy]-1-methyl-3-n-propyl-1,6-dihydro-7H-pyrazolo[4,3-d]pyrimidin-7-one 4-Benzyl-1-piperazinylsulphonyl chloride (Preparation 19, 0.9 g, 0.0029 mol) was added to a stirred solution of 5-(5-amino-2-ethoxyphenyl)-1-methyl-3-n-propyl-1,6-dihydro-7H-pyrazolo[4,3-d]pyrimidin-7-one (0.94 g, 0.0029 mol), 4-dimethylaminopyridine (0.050 g, 0.00041 mol) and triethylamine (1.09 g, 0.0108 mol) in dichloromethane (50 ml). The solution was stirred at room temperature for 48 hours and then evaporated under vacuum. The residue was suspended in saturated aqueous sodium bicarbonate solution (50 ml) and the suspension extracted with dichloromethane (3×30 ml). The organic extracts were combined, washed successively with saturated aqueous sodium bicarbonate solution (2×20 ml) and brine (3×20 ml), dried ($Na_2SO_4$) and evaporated under vacuum. The residue was chromatographed on silica gel (20 g) using a methanol in dichloromethane elution gradient (0–4% methanol), and the required product crystallised from ethyl acetate-hexane to give the title compound as an off-white powder (0.185 g, 11%). Found: C,58.30; H,6.20; N,16.80. $C_{28}H_{35}N_7O_4S$; $0.5H_2O$ requires C,58.52; H,6.31; H,17.06%.

PREPARATION 1

1-Methyl-3-n-propylpyrazole-5-carboxylic acid ethyl ester

A mixture of 3-n-propylpyrazole-5-carboxylic acid ethyl ester (24.1 g, 0.132 mol) (prepared by the method of Chem. Pharm. Bull., 1984, 32, 1568) and dimethyl sulphate (16.8 g, 0.133 mol) were heated to 90° C. for 2.5 hours. The mixture was dissolved in dichloromethane and the solution washed with aqueous sodium carbonate solution. The organic phase was separated, dried (MgSO$_4$) and evaporated under vacuum to give a solid. Chromatography on silica gel (300 g), eluting with dichloromethane, gave the product as a colourless oil (20.4 g, 79%). Rf 0.8 (silica; dichloromethane, methanol, acetic acid; 80:20:1).

PREPARATION 2

1-Methyl-3-n-propylpyrazole-5-carboxylic acid

1-Methyl-3-n-propylpyrazole-5-carboxylic acid ethyl ester (20.2 g, 0.10 mol) was suspended in 6N aqueous sodium hydroxide solution (50 ml, 0.30 mol). The mixture was heated to 80° C. for 2 hours then diluted with water (50 ml) and acidified with concentrated hydrochloric acid (25 ml). Filtration gave the carboxylic acid as pale brown crystals (12.3 g, 71%), m.p. 150°-154° C. Found: C,56.99; H,7.25; N,16.90. C$_8$H$_{12}$N$_2$O$_2$ requires C,57.13; H,7.19; N,16.66%.

PREPARATION 3

1-Methyl-4-nitro-3-n-propylpyrazole-5-carboxylic acid

1-Methyl-3-n-propylpyrazole-5-carboxylic acid (12.1 g, 0.072 mol) was added portionwise to a mixture of oleum (13 ml) and fuming nitric acid (11 ml), keeping the temperature below 60° C. After the addition, the mixture was heated at 60° C. overnight and then cooled to room temperature before being poured onto ice; filtration then gave the nitropyrazole as a white solid (11.5 g, 75%), m.p. 124°-127° C. Found: C,45.43; H,5.22; N,19.42. C$_8$H$_{11}$N$_3$O$_4$ requires C,45.57; H,5.20; N,19.71%.

PREPARATION 4

1-Methyl-4-nitro-3-n-propylpyrazole-5-carboxamide

1-Methyl-4-nitro-3-n-propylpyrazole-5-carboxylic acid (11.3 g, 0.053 mol) was added to thionyl chloride (50 ml) and the resulting mixture heated under reflux for 3 hours. The reaction mixture was then cooled and excess thionyl chloride removed by evaporation under vacuum. The oily residue was dissolved in acetone (50 ml) and the solution cautiously added to a mixture of ice (50 g) and concentrated aqueous ammonium hydroxide solution (50 ml). The precipitate was collected by filtration to provide the pyrazolecarboxamide as a pale yellow solid (8.77 g, 78%), m.p. 141°-143° C. Found: C,45.22; H,5.71; N,26.12. C$_8$H$_{12}$N$_4$O$_3$ requires C,45.28; H,5.70; N,26.40%.

PREPARATION 5

4-Amino1-methyl-3-n-propylpyrazole-5-carboxamide

1-Methyl-4-nitro-3-n-propylpyrazole-5-carboxamide (3.45 g, 16.2 mmol) and stannous chloride dihydrate (18.4 g, 81 mmol) were suspended in ethanol and the mixture heated under reflux for 2 hours. The resulting solution was cooled to room temperature, basified to pH 9 by the addition of 2N aqueous sodium hydroxide solution and extracted with dichloromethane (3×150 ml). The organic extracts were combined, dried (MgSO$_4$) and evaporated under vacuum. Trituration of the residue with ether gave the aminopyrazole as an off-white solid (2.77 g, 94%), m.p. 98°-101° C. Found: C,52.84; H,7.81; N,30.38. C$_8$H$_{14}$N$_4$O requires C,52.73; N,7.74; N,30.75%.

PREPARATION 6

4-(2-Ethoxybenzamido)-1-methyl-3-n-propylpyrazole-5-carboxamide

A solution of 2-ethoxybenzoyl chloride (6.1 g, 33.0 mmol) in dichloromethane (50 ml) was added to a stirred solution of 4-amino-1-methyl-3-n-propylpyrazole-5-carboxamide (3.0 g, 16.4 mmol), 4-dimethylaminopyridine (0.02 g, 0.164 mmol) and triethylamine (3.34 g, 33.0 mmol) in dichloromethane (50 ml) at 0° C. The resulting mixture was allowed to warm to room temperature and stirred for a further 2 hours. The solvent was evaporated under vacuum, the residue dissolved in a 19:1 mixture of dichloromethane and methanol (250 ml), and then the solution washed with 1N hydrochloric acid (100 ml), dried (MgSO$_4$) and evaporated under vacuum. The crude material was chromatographed on silica gel (200 g), eluting with a 97:3 mixture of dichloromethane and methanol, to give a pink solid; crystallisation from ethyl acetate-hexane gave the pyrazole-5-carboxamide as a pale pink solid (2.2 g, 40%), m.p. 153°-155° C. Found: C,61.66; H,6.77; N,16.95. C$_{17}$H$_{22}$N$_4$O$_3$ requires C,61.80; H,6.71; N,16.96%.

PREPARATION 7

5-(2-Ethoxyphenyl)-1-methyl-3-n-propyl-1,6-dihydro-7H-pyrazolo[4,3-d]pyrimidin-7-one 4-(2-Ethoxybenzamido)-1-methyl-3-n-propylpyrazole-5-carboxamide (223 g, 0.676 mol) was added portionwise to a solution of sodium hydroxide (54 g, 1.35 mol) and 30% hydrogen peroxide solution (224 ml) in water (2000 ml). Ethanol (700 ml) was added and the resulting mixture heated under reflux for 2.5 hours, cooled, then evaporated under vacuum. The resulting solid was treated with 2N hydrochloric acid (380 ml), with external cooling, and the mixture was extracted with dichloromethane (1×700 ml, 3×200 ml). The combined organic extracts were washed successively with saturated aqueous sodium carbonate solution (3×400 ml) and brine (300 ml), then dried (Na$_2$SO$_4$) and evaporated under vacuum.

Chromatography of the residue on silica gel (1000 g), using a methanol in dichloromethane elution gradient (0-1% methanol), followed by trituration of the crude product with ether (300 ml), gave the title compound as a colourless solid (152.2 g, 72%), m.p. 143°-146° C. Found: C,65.56; H,6.44; N,18.14. C$_{17}$H$_{20}$N$_4$O$_2$ requires C,65.36; N,6.45; N,17.94%.

PREPARATION 8

5-(5-Bromoacetyl-2-ethoxyphenyl)-1-methyl-3-n-propyl-1,6-dihydro-7H-pyrazolo[4,3-d]pyrimidin-7-one Aluminium trichloride (12.8 g, 0.096 mol) was added portionwise over 1 hour to a stirred solution of 5-(2-ethoxyphenyl)-1-methyl-3-n-propyl-1,6-dihydro-7H-pyrazolo[4,3-d]pyrimidin-7-one (10.0 g, 0.032 mol) and bromoacetyl bromide (5.6 ml, 0.064 mol) in dichloromethane (150 ml) at 0° C. After 18 hours at room temperature, the reaction mixture was poured into ice and water (400 g) and the resulting mixture stirred vigorously. The organic phase was separated and the aqueous phase further extracted with dichloromethane (2×100 ml). The organic solutions were combined, dried (Na$_2$SO$_4$) and evaporated under vacuum to give an off-white solid, trituration of which from ether gave the title compound as a white solid (10.87 g, 78%), m.p. 159°–160° C. Found: C,52.54; H,4.88; N,12.78. C$_{19}$H$_{21}$BrN$_4$O$_3$ requires C,52.67; H,4,88; N,12.93%.

PREPARATION 9

1-Methyl-4-(2-n-propoxybenzamido)-3-n-propyl-pyrazole-5-carboxamide

This amide was prepared from 2-n-propoxybenzoyl chloride following the procedure described in Preparation 6 and was obtained as a pink solid (63%), m.p. 148°–149° C. Found: C,62.97; H,7.00; N,16.29. C$_{18}$H$_{24}$N$_4$O$_3$ requires C,62.77; H,7.02; N,16.27%.

PREPARATION 10

1-Methyl-5-(2-n-propoxyphenyl)-3-n-propyl-1,6-dihydro-7H-pyrazolo[4,3-d]pyrimidin-7-one 1-Methyl-4-(2-n-propoxybenzamido)-3-n-propyl-pyrazole-5-carboxamide (0.34 g, 0.99 mmol) was added to a stirred mixture of 30% hydrogen peroxide solution (1.0 ml), potassium carbonate (0.54 g, 3.92 mmol), water (10 ml) and ethanol (5 ml). The mixture was heated under reflux for 38 hours and then evaporated under vacuum. The residue was suspended in water (20 ml), then the suspension acidified with 2N hydrochloric acid and extracted with dichloromethane (3×20 ml). The extracts were combined, dried (Na$_2$SO$_4$) and evaporated under vacuum. The resulting residue was chromatographed on silica gel (6 g), using a methanol in dichloromethane elution gradient (0–1% methanol), to give an oil, successive trituration of which with ether gave the required product as a white solid (0.19 g, 59%), m.p. 111°–114° C. Found: C,66.26; H,6.92; N,17.15. C$_{18}$H$_{22}$N$_4$O$_2$ requires C,66.23; H,6.80; N,17.17%.

PREPARATION 11

5-(5-Bromoacetyl-2-n-propoxyphenyl)-1-methyl-3-n-propyl-1,6-dihydro-7H-pyrazolo[4,3-d]pyrimidin-7-one Aluminium trichloride (6.0 g, 0.045 mol) was added portionwise to a stirred solution of 1-methyl-5-(2-n-propoxyphenyl)-3-n-propyl-1,6-dihydro-7H-pyrazolo[4,3-d]pyrimidin-7-one (5.0 g, 0.0153 mol) and 2-bromoacetyl chloride (2.5 ml, 0.0303 mol) in dichloromethane (100 ml) at 0° C. The reaction mixture was allowed to warm to room temperature, stirred for 18 hours, heated under reflux for 3 hours and then added cautiously to ice and water (100 g). The resulting mixture was stirred for 1 hour and extracted with dichloromethane (2×50 ml). The combined organic extracts were washed with brine (2×50 ml), dried (Na$_2$SO$_4$), then evaporated under vacuum to give an off-white solid, which was triturated with ether to give the title compound as a white solid (4.1 g, 60%). A small sample was crystallised from ethyl acetate-hexane to give the pure product, m.p. 136°–137° C. Found: C,53.82; H,5.24; N,12.57. C$_{20}$H$_{23}$BrN$_4$O$_3$ requires C,53.70; H,5.18; N,12.52%.

PREPARATION 12

5-Acetyl-2-ethoxybenzoic acid methyl ester

Iodoethane (16.4 g, 0.105 mol) was added to a stirred mixture of 5-acetyl-2-hydroxybenzoic acid methyl ester (10 g, 51.5 mol) and anhydrous potassium carbonate (14.4 g, 0.104 mol) in 2-butane (200 ml) and the resulting mixture heated under reflux for 3 days. The solvent was removed by evaporation under vacuum and the residue partitioned between water (100 ml) and ethyl acetate (100 ml). The aqueous phase was removed and extracted with further ethyl acetate (4×100 ml). The organic solutions were combined, dried (Na$_2$SO$_4$) and evaporated under vacuum. The residue was chromatographed on silica gel (130 g), using a methanol in dichloromethane elution gradient (0–1% methanol), to give the title compound as colourless crystals (10.15 g, 89%), m.p. 50°–55° C. Found: C,64.88; H,6.38. C$_{12}$H$_{14}$O$_4$ requires C,64.85; H,6.35%.

PREPARATION 13

5-Acetyl-2-ethoxybenzoic acid

A mixture of 5-acetyl-2-ethoxybenzoic acid methyl ester (9.6 g, 0.043 mol), 5M aqueous sodium hydroxide solution (44 ml, 0.217 mol), water (80 ml) and 1,4-dioxan (80 ml) was stirred at room temperature for 18 hours. The solvent was removed by evaporation under vacuum, the residue dissolved in water (100 ml) and the resulting solution acidified to pH 1 with concentrated hydrochloric acid. The aqueous mixture was extracted with ethyl acetate (4×100 ml) and the combined extracts dried (Na$_2$SO$_4$) and evaporated under vacuum. The resulting solid was crystallised from ethyl acetate to give the title compound as a colourless solid (5.4 g, 60%), m.p. 122°–135° C. Found: C,63.20; H,5.81. C$_{11}$H$_{12}$O$_4$ requires C,63.45; H,5.81%.

PREPARATION 14

5-Acetyl-2-ethoxybenzoyl chloride

Oxalyl chloride (3.66 g, 0.029 mol) was added dropwise to a stirred solution of 5-acetyl-2-ethoxybenzoic acid (3.0 g, 0.014 mol) in dichloromethane (15 ml) and dimethylformamide (0.1 ml). After 3 hours at room temperature, the solvent was removed by evaporation under vacuum and the residue azeotroped with hexane (3×30 ml) to give the title compound, which was used without further purification.

PREPARATION 15

4-(5-Acetyl-2-ethoxybenzamido)-1-methyl-3-n-propyl-pyrazole-5-carboxamide

The title compound was prepared from 5-acetyl-2-ethoxybenzoyl chloride and 4-amino-1-methyl-3-n-propylpyrazole-5-carboxamide following the procedure of Preparation 6, and was obtained as a white solid (60%), m.p. 225°–227° C. Found: C,61.35; H,6.25; N,15.07. C$_{19}$H$_{24}$N$_4$O$_4$ requires C,61.28; H,6.50; N,15.04%.

PREPARATION 16

5-(5-Chloromethyl-2-n-propoxyphenyl)-1-methyl-3-n-propyl-1,6-dihydro-7H-pyrazolo[4,3-d]pyrimidin-7-one 1-Methyl-5-(2-n-propoxyphenyl)-3-n-propyl-1,6-dihydro-7H-pyrazolo[4,3-d]pyrimidin-7-one (0.80 g, 0.00246 mol) was added portionwise to stirred concentrated hydrochloric acid (10 ml) at room temperature.

Paraformaldehyde (0.20 g, 0.00246 mol) was then added and the resulting solution stirred at 120° C. for 22 hours. The reaction mixture was cooled and poured into ice and water (50 g), then the resulting mixture extracted with ethyl acetate (3×30 ml). The organic extracts were combined, dried (Na$_2$SO$_4$) and evaporated under vacuum to give a white solid. Trituration with ether, followed by crystallisation from ethyl acetate-hexane, gave the title compound as colourless crystals (0.65 g, 70%), m.p. 102°–104° C. Found: C,60.91; H,6.14; N,14.94. C$_{19}$H$_{23}$ClN$_4$O$_2$ requires C,60.88; H,6.18; N,14.95%.

PREPARATION 17

5-(2-Ethoxy-5-nitrophenyl)-1-methyl-3-n-propyl-1,6-dihydro-7H-pyrazolo[4,3-d]pyrimidin-7-one Concentrated nitric acid (0.5 ml) was added dropwise to a stirred solution of 5-(2-ethoxyphenyl)-1-methyl-3-n-propyl-1,6-dihydro-7H-pyrazolo[4,3-d]pyrimidin-7-one (2.0 g, 0.0064 mol) in concentrated sulphuric acid (10 ml) at 0° C., and the resulting orange solution was stirred at room temperature for 18 hours. The reaction solution was then added dropwise to stirred ice and water (200 g) and the solid precipitate collected by filtration. This solid was then dissolved in dichloromethane (50 ml) and the solution washed succesively with brine (2×30 ml) and water (30 ml), dried (Na$_2$SO$_4$) and evaporated under vacuum to give a yellow solid. Crystallisation from acetonitrile gave the title compound as yellow needles (1.40 g, 61%), m.p. 214°–216° C. Found: C,57.36; H,5.21; H,19.49. C$_{17}$H$_{19}$N$_5$O$_4$ requires C,57.13; H,5.36; N,19.60%.

PREPARATION 18

5-(5-Amino-2-ethoxyphenyl)-1-methyl-3-n-propyl-1,6-dihydro-7H-pyrazolo[4,3-d]pyrimidin-7-one 5-(2-Ethoxy-5-nitrophenyl)-1-methyl-3-n-propyl-1,6-dihydro-7H-pyrazolo[4,3-d]pyrimidin-7-one (0.64 g, 0.0018 mol) was dissolved in ethanol (50 ml) and the solution stirred with 5% palladium on charcoal catalyst (0.050 g) under hydrogen at room temperature and 50 p.s.i. pressure for 4 hours. The mixture was filtered to remove the catalyst, the filtrate evaporated under vacuum, and the residue triturated with ether to give the title compound as an off-white solid (0.56 g, 95%), m.p. 147°–148° C. Found: C,62.63; H,6.60; N,21.57. C$_{17}$H$_{21}$N$_5$O$_2$ requires C,62.36; H,6.47; N,21.39%.

PREPARATION 19

4-Benzyl-1-piperazinylsulphonyl chloride

A solution of 1-benzylpiperazine (20.0 g, 0.114 mol) in acetonitrile (45 ml) was added to a solution of sulphuryl chloride (28 ml, 0.346 mol) in acetonitrile (50 ml) and the mixture heated under reflux for 17 hours, then cooled. The solvent was removed by evaporation under vacuum, then the residue triturated with ether (20×50 ml) to yield the title compound (27.8 g, 89%), which was used without further purification.

Biological Activity

The following Table illustrates the in vitro activities for a range of the compounds of the invention.

TABLE

IN VITRO PDE INHIBITORY DATA: SELECTIVITY BETWEEN CALCIUM/CALMODULIN (Ca/CAM)-INDEPENDENT cGMP PDE AND cGMP-INHIBITED cAMP PDE

| EXAMPLE | IC$_{50}$(nM) cGMP | cAMP | SELECTIVITY RATIO |
|---|---|---|---|
| 3 | 2.2 | 86,000 | 39,090 |
| 4 | 1.8 | 63,000 | 35,000 |
| 11 | 4.9 | 57,000 | 11,632 |
| 14 | 1.0 | 57,000 | 57,000 |
| 15 | 3.4 | 75,000 | 22,058 |
| 16 | 3.7 | 53,000 | 14,324 |
| 20 | 3.7 | 59,000 | 15,945 |
| 25 | 3.4 | 84,000 | 24,705 |
| 29 | 5.5 | 84,000 | 15,272 |
| 30 | 1.4 | 58,000 | 41,428 |
| 31 | 3.4 | 56,000 | 16,470 |
| 32 | 1.4 | 38,000 | 27,142 |
| 39 | 5.3 | 54,000 | 10,188 |

Safety Profile

Certain compounds of the invention have been tested at therapeutic doses of up to 1 mg/Kg i.v. and up to 3 mg/Kg p.o. in rats with no signs of adverse acute toxicity being observed. In mice, no deaths occurred after doses of up to 100 mg/Kg i.v.

We claim:

1. A method of treating stroke, peripheral vascular disease, conditions of reduced blood vessel patency, chronic asthma, bronchitis, allergic asthma or allergic rhinitis in a human in need of such treatment comprising administering to said human an effective amount of a compound of formula:

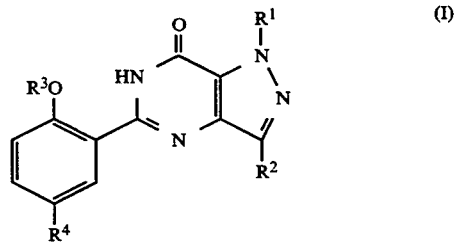

or a pharmaceutically acceptable salt thereof, wherein

R$^1$ is H; C$_1$–C$_3$ alkyl optionally substituted with one or more fluoro substituents; or C$_3$–C$_5$ cycloalkyl;

R$^2$ is H, or C$_1$–C$_6$ alkyl optionally substituted with one or more fluoro substituents or with C$_3$–C$_6$ cycloalkyl;

R$^3$ is C$_1$–C$_6$ alkyl optionally substituted with one or more fluoro substituents or with C$_3$–C$_6$ cycloalkyl; C$_3$–C$_5$ cycloalkyl; C$_3$–C$_6$ alkenyl; or C$_3$–C$_6$ alkynyl;

R$^4$ is C$_1$–C$_4$ alkyl substituted with OH, NR$^5$R$^6$, CN, CONR$^5$R$^6$ or CO$_2$R$^7$; C$_2$–C$_4$ alkenyl optionally substituted with CN, CONR$^5$R$^6$ or CO$_2$R$^7$; C$_2$–C$_4$ alkanoyl optionally substituted with NR$^5$R$^6$; hydroxy C$_2$–C$_4$ alkyl optionally substituted with NR$^5$R$^6$; (C$_2$–C$_3$ alkoxy)C$_1$–C$_2$ alkyl optionally substituted with OH or NR$^5$R$^6$; CONR$^5$R$^6$; CO$_2$R$^7$; NHSO$_2$NR$^5$R$^6$; NHSO$_2$R$^8$; or phenyl, thienyl, pyridyl, imidazolyl, triazolyl, oxazolyl, thiazolyl or pyrimidinyl any of which is optionally substituted with methyl;

R$^5$ and R$^6$ are each independently H or C$_1$–C$_4$ alkyl, or together with the nitrogen atom to which they are attached form a pyrrolidinyl, piperidino, morpholino, 4-($NR^9$)-piperazinyl or imidazolyl group wherein said group is optionally substituted with methyl or hydroxy;

$R^7$ is H or $C_1$-$C_4$ alkyl;

$R^8$ is $C_1$-$C_3$ alkyl optionally substituted with $NR^5R^6$; and $R^9$ is H; $C_1$-$C_3$ alkyl optionally substituted with phenyl; hydroxy $C_2$-$C_3$ alkyl; or $C_1$-$C_4$ alkanoyl.

2. A method of preventing stroke, peripheral vascular disease, conditions of reduced blood vessel patency, chromic asthma, bronchitis, allergic asthma or allergic rhinitis in a human in need of such treatment comprising administering to said human an effective amount of a compound of formula

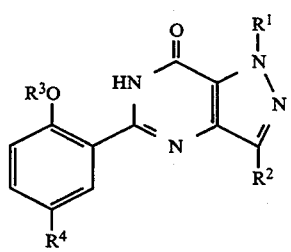

(I)

or a pharmaceutically acceptable salt thereof, wherein $R^1$ is H; $C_1$-$C_3$ alkyl optionally substituted with one or more fluoro substituents; or $C_3$-$C_5$ cycloalkyl;

$R^2$ is H, or $C_1$-$C_6$ alkyl optionally substituted with one or more fluoro substituents or with $C_3$-$C_6$ cycloalkyl;

$R^3$ is $C_1$-$C_6$ alkyl optionally substituted with one or more fluoro substituents or with $C_3$-$C_6$ cycloalkyl; $C_3$-$C_5$ cycloalkyl; $C_3$-$C_6$ alkenyl; or $C_3$-$C_6$ alkynyl;

$R^4$ is $C_1$-$C_4$ alkyl substituted with OH, $NR^5R^6$, CN, $CONR^5R^6$ or $CO_2R^7$; $C_2$-$C_4$ alkenyl optionally substituted with CN, $CONR^5R^6$ or $CO_2R^7$; $C_2$-$C_4$ alkanoyl optionally substituted with $NR^5R^6$; hydroxy $C_2$-$C_4$ alkyl optionally substituted with $NR^5R^6$; ($C_2$-$C_3$ alkoxy)$C_1$-$C_2$ alkyl optionally substituted with OH or $NR^5R^6$; $CONR^5R^6$; $CO_2R^7$; $NHSO_2NR^5R^6$; $NHSO_2R^8$; or phenyl, thienyl, pyridyl, imidazolyl, triazolyl, oxazolyl, thiazolyl or pyrimidinyl any of which is optionally substituted with methyl;

$R^5$ and $R^6$ are each independently H or $C_1$-$C_4$ alkyl, or together with the nitrogen atom to which they are attached form a pyrrolidinyl, piperidino, morpholino, 4-($NR^9$)-piperazinyl or imidazolyl group wherein said group is optionally substituted with methyl or hydroxy;

$R^7$ is H or $C_1$-$C_4$ alkyl;

$R^8$ is $C_1$-$C_3$ alkyl optionally substituted with $NR^5R^6$; and $R^9$ is H; $C_1$-$C_3$ alkyl optionally substituted with phenyl; hydroxy $C_2$-$C_3$ alkyl; or $C_1$-$C_4$ alkanoyl.

* * * * *

UNITED STATES PATENT AND TRADEMARK OFFICE
CERTIFICATE OF CORRECTION

PATENT NO. : 5,426,107

DATED : June 20, 1995

INVENTOR(S) : Andrew S. Bell and Nicholas K. Terrett

It is certified that error appears in the above-identified patent and that said Letters Patent is hereby corrected as shown below:

At column 5, line 51, "CH"

should read --OH--;

At column 11, line 2, "1979"

should read --1971-- ;

At column 15, line 59, "["

should read --]--;

At column 17, line 13, "N,5.22"

should read --"H,5.22--;

At column 20, line 36, "0.0051 mol"

should read --0.00051 mol--;

At column 21, line 23, "5-[Ethoxy-5-(2-pyridyl)phenyl-1-methyl-3-n-propyl-1,6-dihydro-7H-pyrazolo[4,3-d]pyrimidin-7-one"

should read --5-[Ethoxy-5-(2-pyridyl)phenyl]-1-methyl-3-n-propyl-1,6-dihydro-7H-pyrazolo[4,3-d]pyrimidin-7-one--;

UNITED STATES PATENT AND TRADEMARK OFFICE
CERTIFICATE OF CORRECTION

Page 2 of 2

PATENT NO. : 5,426,107
DATED : June 20, 1995
INVENTOR(S) : Andrew S. Bell, et. al.

It is certified that error appears in the above-indentified patent and that said Letters Patent is hereby corrected as shown below:

At column 23, line 36, "H, 11.69" should read --N,11.69--;

Signed and Sealed this

Twenty-first Day of November, 1995

Attest:

BRUCE LEHMAN

Attesting Officer

Commissioner of Patents and Trademarks